(12) United States Patent
Kisak et al.

(10) Patent No.: US 8,343,962 B2
(45) Date of Patent: *Jan. 1, 2013

(54) TOPICAL FORMULATION

(75) Inventors: Edward T. Kisak, San Diego, CA (US); John M. Newsam, La Jolla, CA (US); Dominic King-Smith, San Diego, CA (US); Pankaj Karande, Troy, NY (US); Samir Mitragotri, Goleta, CA (US)

(73) Assignee: Nuvo Research Inc., Mississagua, Ontario (CA)

( * ) Notice: Subject to any disclaimer, the term of this patent is extended or adjusted under 35 U.S.C. 154(b) by 212 days.

This patent is subject to a terminal disclaimer.

(21) Appl. No.: 12/848,792

(22) Filed: Aug. 2, 2010

(65) Prior Publication Data

US 2011/0028460 A1 Feb. 3, 2011

Related U.S. Application Data

(63) Continuation-in-part of application No. 12/281,561, filed as application No. PCT/IB2007/001983 on Mar. 6, 2007, now Pat. No. 7,795,309.

(60) Provisional application No. 60/778,847, filed on Mar. 6, 2006.

(51) Int. Cl.
| | |
|---|---|
| *A61K 31/19* | (2006.01) |
| *A61K 31/195* | (2006.01) |
| *A61K 31/40* | (2006.01) |
| *A61K 31/444* | (2006.01) |
| *A61K 31/5415* | (2006.01) |

(52) U.S. Cl. .................... 514/226.5; 514/334; 514/420; 514/557; 514/567

(58) Field of Classification Search ............... 514/226.5, 514/334, 420, 557, 567
See application file for complete search history.

(56) References Cited

U.S. PATENT DOCUMENTS

| | | | |
|---|---|---|---|
| 5,602,183 | A | 2/1997 | Martin et al. |
| 5,648,380 | A | 7/1997 | Martin |
| 5,874,479 | A | 2/1999 | Martin |
| 6,328,979 | B1 | 12/2001 | Yamashita et al. |
| 7,001,592 | B1 | 2/2006 | Traynor et al. |
| 7,795,309 | B2 | 9/2010 | Kisak et al. |
| 2002/0064524 | A1 | 5/2002 | Cevc |

FOREIGN PATENT DOCUMENTS

WO WO 2005/009510 2/2005

OTHER PUBLICATIONS

International Search Report issued on Aug. 8, 2008 in application No. PCT/IB2007/01983 (corresponding to US 7,795,309).
Notice of Allowance issued on Apr. 29, 2010 by the Examiner in U.S. Appl. No. 12/281,561 (US 7,795,309).
Office Action issued on Dec. 30, 2009 by the Examiner in U.S. Appl. No. 12/281,561 (US 7,795,309).

*Primary Examiner* — Raymond Henley, III
(74) *Attorney, Agent, or Firm* — Foley & Lardner LLP

(57) ABSTRACT

It has been discovered that certain combinations compounds are excellent penetration enhancers and, as such, can be incorporated in a topical formulation to facilitate administration of active agents. The increased penetration enhancement can also lead to a reduction in the total concentration of skin irritants in the formulation. There is described herein a topical formulation comprising (i) at least one active agent; (ii) a first compound, and (iii) a second compound, wherein the first compound and second compound are different, and each is selected from the group consisting of N-lauroyl sarcosine, sodium octyl sulfate, methyl laurate, isopropyl myristate, oleic acid, glyceryl oleate and sodium lauryl sulfoacetate.

29 Claims, No Drawings

TOPICAL FORMULATION

CROSS-REFERENCE TO RELATED APPLICATIONS

This application is a continuation in part of U.S. application Ser. No. 12/281,561, filed on Jan. 12, 2009, now U.S. Pat. No. 7,795,309, which is a national stage of PCT/IB2007/001983, filed on Mar. 6, 2007, which claims priority to U.S. Provisional Application No. 60/778,847, filed on Mar. 6, 2006, the entire contents and disclosures of each of which are hereby incorporated by reference.

FIELD OF THE INVENTION

The present invention relates to a topical formulation of multiplexed molecular penetration enhancers. In a particularly preferred embodiment, the present invention relates to a topical formulation of multiplexed molecular penetration enhancers for topical or transdermal administration of one or more active ingredients such as a pharmaceutical agent.

DESCRIPTION OF THE PRIOR ART

Topical formulations for application to the skin can be useful in cosmetic applications, for treating conditions of the upper skin layers and for transdermal administration of active agents to the local tissue underlying the skin or into the blood for systemic distribution. Use of a topical formulation of, for instance, a pharmaceutical agent is advantageous in that it avoids firstpass metabolism, circumvents gastrointestinal ("GI") absorption, can allow delivery of an active ingredient with a relatively short biological half-life and/or a narrow therapeutic window and facilitates uniform plasma dosing of the active ingredient, and/or can improve user compliance.

In spite of the advantages, transdermal administration is usually limited to about a dozen small lipophilic drugs, available in transdermal patch format (including scopolamine, fentanyl, estradiol, nitroglycerine, nicotine and testosterone).

Skin has evolved to impede the flux of exogenous molecules so as to provide a strong barrier to molecular delivery, particularly agents such as pharmaceutical agents. Transdermal drug administration is difficult since skin is an excellent diffusion barrier.

Structurally, the skin consists of two principle parts: (i) a relatively thin outermost layer (the 'epidermis'), and (ii) a thicker inner region (the 'dermis'). The outermost layer of the epidermis (the 'stratum corneum') consists of flattened dead cells which are filled with keratin. The region between the flattened dead cells of the stratum corneum is filled with lipids which form lamellar phases. The highly impermeable nature of skin is due primarily to the stratum corneum. The viable epidermis underlying the stratum corneum is akin to other living tissue. The dermis provides the skin's structural strength as well as the nerve and vascular networks that support the epidermis.

Delivering an active agent into or through the skin in sufficient concentrations often requires some means for reducing the stratum corneum's hindrance of penetration. A number of methods for lowering the stratum corneum's barrier properties have been developed, including electrically assisted techniques such as iontophoresis or ultrasound, and bypassing the stratum corneum through microneedle arrays or ablation.

Molecular or chemical penetration enhancers provide an effective and inexpensive means of temporarily reducing skin resistance to the passage of actives and other molecules. Molecular penetration enhancers or 'MPE™'s' can enhance the diffusion of molecules across the skin by, for example, disrupting the lipid bilayers of the stratum corneum.

Over 300 substances have been identified as MPE™s but surprisingly few have been successfully developed into commercial formulations. Many potent MPE™s are irritating to the cells of the epidermis which can limit both the choice and concentration of MPE™s suitable for topical formulations.

Discovery of new MPE™'s to increase skin permeability is highly desirable and has been an area of high activity over the last 30 years. However, the number of substances identified to be penetration enhancers is still small relative to the more than 25,000,000 substances identified in the CAS registry (Chemical Abstracts Service, Columbus, Ohio, www.cas.orq).

The number of candidate drugs suitable for topical and transdermal administration could be significantly increased with improved penetration enhancers.

One example of a commercialized formulation for use in transdermal administration is described in U.S. Pat. No. 4,575,515 [Sandborn]. Sandborn teaches a formulation that includes a medicine and dimethyl sulfoxide (DMSO), and that purportedly allows for rapid and deep penetration of the medicine into the underlying tissue.

While the topical formulation taught by Sandborn represents an advance in the art, there is room for improvement. For instance the formulation taught by Sandborn contains a relatively high concentration of DMSO, which is known to cause skin irritation. In particular there is a need for a topical formulation having improved flux of the active ingredient through the skin as compared to the topical formulation taught by Sandborn.

SUMMARY OF THE INVENTION

It is an object of the present invention to provide a novel topical formulation.

It is another object of the present invention to provide a novel topical formulation for topical or transdermal administration of an active agent.

It is another object of the present invention to provide a topical formulation capable of providing improved fluxes of therapeutically active agents and other molecules through the skin as compared to the topical formulation taught by Sandborn.

Accordingly, in one of its aspects, the present invention provides a topical formulation comprising: (i) at least one active agent, (ii) a first compound, and (iii) a second compound, wherein the first compound and second compound are different, and each is selected from the group of MPE™s consisting of N-lauroyl sarcosine, sodium octyl sulfate, methyl laurate, isopropyl myristate, oleic acid, glyceryl oleate and sodium lauryl sulfoacetate.

In another of its aspects, the present invention provides a topical formulation for use in topical or transdermal administration of a substance comprising: (i) at least one active agent, (ii) a first compound, (iii) a second compound, and (iv) a therapeutically acceptable carrier that is different from the first compound and the second compound, wherein the first compound and second compound are different, and each is selected from the group of MPE™s consisting of N-lauroyl sarcosine, sodium octyl sulfate, methyl laurate, isopropyl myristate, oleic acid, glyceryl oleate and sodium lauryl sulfoacetate.

In yet another of its aspects, the present invention provides a topical formulation comprising a therapeutically active agent, a therapeutically acceptable carrier and a skin penetration enhancer, wherein the skin penetration enhancer consists essentially of a mixture of N-lauroyl sarcosine and oleic acid.

DETAILED DESCRIPTION OF THE PREFERRED EMBODIMENTS

The present invention provides a topical formulation that may be used for the topical or transdermal administration of at least one active agent. As used throughout this specification, the term 'transdermal" means in the broadest sense through the skin. Further the terms 'transdermal' and 'percutaneous' are used interchangeably throughout this specification.

As used herein the term 'topical formulation' refers to a formulation that may be applied to skin or a mucosa. Topical formulations may, for example, be used to confer therapeutic benefit to a patient or cosmetic benefits to a consumer. Topical formulations can be used for both topical and transdermal administration of substances.

The term 'topical administration' is used in its conventional sense to mean delivery of a substance, such as a therapeutically active agent, to the skin or a localized region of the body. Topical administration of a drug may often be advantageously applied in, for example, the treatment of various skin disorders.

The term 'transdermal administration' is used to mean administration through the skin. Transdermal administration is often applied where systemic delivery of an active is desired, although it may also be useful for delivering an active to tissues underlying the skin with minimal systemic absorption.

The term 'penetration enhancer' is used herein to refer to an agent that improves the transport of molecules such as an active agent (e.g., a medicine) into or through the skin. Various conditions may occur at different sites in the body either in the skin or below creating a need to target delivery of compounds. For example, in products designed to produce artificial tans, delivery of dye substances into the stratum corneum may be advantageous. A psoriasis treatment on the other hand may require delivery of therapeutic drug levels in deeper epidermal tissue. In a treatment for osteoarthritis, delivery of the active agent into deeper underlying joint tissue may be necessary to achieve therapeutic benefit. In yet other applications, for example in hormone replacement therapy, delivery of drug to the systemic circulation may be an objective. Thus, a 'penetration enhancer' may be used to assist in the delivery of an active agent directly to the skin or underlying tissue or indirectly to the site of the disease through systemic distribution. A penetration enhancer may be a pure substance or may comprise a mixture of different chemical entities. In this specification the terms 'penetration enhancer', 'chemical penetration enhancer', 'molecular penetration enhancer' and 'MPE™' are used interchangeably.

As used herein the term 'multiplexed molecular penetration enhancers' ("MMPE™") means a penetration enhancer comprising two or more substances wherein each of the two or more substances is also penetration enhancer.

The present inventors have surprisingly and unexpectedly discovered that certain combination of compounds are excellent penetration enhancers and, as such, can be incorporated in a topical formulation to facilitate administration of one or more active ingredients. The increased penetration enhancement can also lead to a reduction in the total concentration of skin irritants in a formulation.

The compounds acting as excellent penetration enhancers are used in combination—i.e., two (or more) compounds are selected from wherein the first compound and second compound are different, and each is selected from the group consisting essentially of N-lauroyl sarcosine, sodium octyl sulfate, methyl laurate, isopropyl myristate, oleic acid, glyceryl oleate and sodium lauryl sulfoacetate.

The preferred combinations of compounds that act as improved penetration enhancers include the following:
 the first compound comprises N-lauroyl sarcosine and the second compound comprises isopropyl myristate;
 the first compound comprises N-lauroyl sarcosine and the second compound comprises oleic acid;
 the first compound comprises sodium octyl sulfate and the second compound comprises oleic acid;
 the first compound comprises glyceryl oleate and the second compound comprises sodium octyl sulfate;
 the first compound comprises glyceryl oleate and the second compound comprises methyl laurate;
 the first compound comprises sodium lauryl sulfoacetate and the second compound comprises methyl laurate; and
 the first compound comprises sodium lauryl sulfoacetate and the second compound comprises isopropyl myristate.

Preferably, the weight ratio of the first compound to the second compound is in the range of from about 1:9 to about 9:1. More preferably, the weight ratio of the first compound to the second compound is in the range of from about 1:4 to about 4:1. Even more preferably, the weight ratio of the first compound to the second compound is in the range of from about 1:3 to about 3:1. Even more preferably, the weight ratio of the first compound to the second compound is in the range of from about 1:2 to about 2:1. Most preferably, the weight ratio of the first compound to the second compound is about 1:1.

Preferably, the total concentration of the first compound and the second compound is up to about 50 wt. % per unit volume of the formulation. More preferably, the total concentration of the first compound and the second compound is up to about 40 wt. % per unit volume of the formulation. Even more preferably, the total concentration of the first compound and the second compound is in the range of from about 1 to about to about 35 wt. % per unit volume of the formulation. Even more preferably, the total concentration of the first compound and the second compound is in the range of from about 1 to about to about 30 wt. % per unit volume of the formulation. Even more preferably, the total concentration of the first compound and the second compound is in the range of from about 1 to about to about 25 wt. % per unit volume of the formulation. Even more preferably, the total concentration of the first compound and the second compound is in the range of from about 1 to about to about 20 wt. % per unit volume of the formulation. Even more preferably, the total concentration of the first compound and the second compound is in the range of from about 1 to about to about 15 wt. % per unit volume of the formulation. Even more preferably, the total concentration of the first compound and the second compound is in the range of from about 1 to about to about 10 wt. % per unit volume of the formulation. Even more preferably, the total concentration of the first compound and the second compound is in the range of from about 1 to about to about 7.5 wt. % per unit volume of the formulation. Even more preferably, the total concentration of the first compound and the second compound is in the range of from about 1 to about to about 5 wt. % per unit volume of the formulation.

Most preferably, the total concentration of the first compound and the second compound is in the range of from about 2 to about to about 5 wt. % per unit volume of the formulation. Within this most preferred embodiment, it can, in some cases, be preferable to have the total concentration of the first compound and the second compound in the range of from about 2 to about to about 4 wt. % per unit volume of the formulation.

In one aspect of the present invention, the at least one active agent is an aryl alkanoic acid, such as an α-aryl alkanoic acid. As is known to a person skilled in the art, α-aryl alkanoic acids are chemical compounds having the general structure of Formula I:

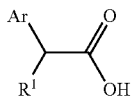

I wherein Ar is an aryl group and $R^1$ is H or an alkyl group, wherein aryl includes aromatic and heteroaromatic groups and alkyl includes acyclic and cyclic alkyl groups. The α-aryl alkanoic acid may be an anti-inflammatory drug such as a non-steroidal anti-inflammatory drug (NSAID) or an analgesic, specific examples of which are listed below. Preferably, the α-aryl alkanoic acids is selected from the group consisting of bromfenac, diclofenac, fenoprofen, flurbiprofen, ibuprofen, indomethacin, ketoprofen, ketorolac, naproxen, sulindac and tolmetin, and pharmaceutically acceptable salts and solvates thereof and mixtures thereof. Structures for these α-aryl alkanoic acids, along with some common trade names, known to a person skilled in the art, are shown in Table 1. More preferably the α-aryl alkanoic acid is selected from the group consisting of diclofenac, ibuprofen and ketoprofen, and pharmaceutically acceptable salts and solvates thereof, and mixtures thereof. Other NSAIDs, that are not α-aryl alkanoic acids, as well as other compounds having antipyretic and analgesic actions are also included in the scope of the present invention. Examples of such compounds include, acetaminophen (paracetamol), aspirin, celecoxib, diflunisal, etodolac, etoricoxib, meclofenamic acid, mefenamic acid, meloxicam, nabumetone, oxaprozin, piroxicam, salsalate, and rofecoxib. Structures for these compounds along with some common trade names, known to a person skilled in the art, are shown in Table 2.

In another aspect of the present invention, the at least one active agent is a phenethylamine, for example, a phenethylamine that is an antidepressant, anti-anxiety agent, anticholinergic agent, cholinergic, dopaminergic, stimulant, serotonin antiagonist, serotonin inhibitor, anti-emetic, antihistamine and/or antipsychotic, specific examples of which are listed below. As is known to a person skilled in the art, phenethylamines are chemical compounds having the general core structure of Formula II:

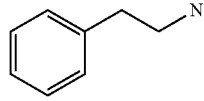

II wherein the phenyl ring, ethylene chain and nitrogen can be substituted. The phenethylamine may be a psychoactive agent that exerts its effect through a monoamine neurotransmitter system, for example dopamine, serotonin and/or norepinephrine receptors. Examples of phenethylamines, include, for example, bupropion, amphetamine, hydroxyamphetamine, dextroamphetamine, methamphetamine, ephedrine, epinephrine, pseudoephedrine, dopamine, epinephryl borate, etafedrine, norepinephrine and oxidopamine, and pharmaceutically acceptable salts and solvates thereof, and mixtures thereof. Preferably the phenethylamine is bupropion, or a pharmaceutically acceptable salt or solvate thereof, such as bupropion hydrochloride. The structure of bupropion, known to a person skilled in the art, is:

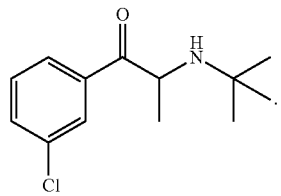 [SMILES: CC(NC(C)(C)C)C(=O)c1cccc(Cl)c1]

In another aspect of the present invention, the at least one active agent is a steroid, for example, steroids that are hormones, glucosteroids, androgens, adrenocortical steroids, anabolics, estrogens and/or progestin, specific examples of which are listed below. As known to a person skilled in the art, steroids are a class of compounds having as a core structure, 4 rings joined as shown in Formula III:

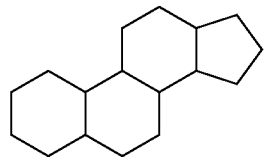

III wherein the carbon atoms are optionally substituted. Preferably the steroid is testosterone, or a pharmaceutically acceptable salt or solvate thereof.

Other suitable active agents include those in the class of COX-2 inhibitors such as celecoxib, rofecoxib, valdecoxib, lumiracoxib, etoricoxib; Antifungals such as tolnaftate, econazole, ciclopirox; Antibiotics such as clindamycin; Musculoskeletal agents such as dantrolene; Retinoids such as isotretinoin; Antivirals such as acyclovir; Vasodilating agents such as nitroglycerine, papaverine; Hormones and synthetic substitutes such as androgens, estrogens, insulin; Opiate agonist such as fentanyl, oxycodone, hydromorphone; Local Anaesthetics such as lidocaine, tocainide and mexiletine and butyl-para-aminobenzoate; Anti-inflammatories such as corticosteroids; NMDA receptor antagonists such as ketamine, dextromethorphan and amantadine.

Examples of other therapeutically active agents that may be used include the following: adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic; antinauseant; antineoplastic; antineutropenic; antiparasitic; antiproliferative; antipsychotic; antirheumatic; antiseborrheic; antisecretory; antispasmodic; antithrombotic; antiulcerative; antiviral; appetite suppressant; blood glucose regulator; bone resorption inhibitor; bronchodilator; cardiovascular agent; cholinergic;

depressant; diagnostic aid; diuretic; dopaminergic agent; estrogen receptor agonist; fibrinolytic; fluorescent agent; free oxygen radical scavenger; gastric acid suppressant; gastrointestinal motility effector; glucocorticoid; hair growth stimulant; hemostatic; histamine H2 receptor antagonists; hormone; hypocholesterolemic; hypoglycemic, hypolipidemic; hypotensive; imaging agent; immunizing agent; immunomodulator; immunoregulator; immunostimulant; immunosuppressant, keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine Al antagonist; serotonin antagonist; serotonin inhibitor; serotonin receptor antagonist; steroid; thyroid hormone; thyroid inhibitor; thyromimetic, tranquilizer; amyotrophic lateral sclerosis agent; cerebral ischemia agent; Paget's disease agent; unstable angina agent; vasoconstrictor; vasodilator; wound healing agent; xanthine oxidase inhibitor; and the like.

Specific examples of pharmaceutical agents that may be included within the present topical formulation, both alone or in combination, include but are not limited to:

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; and Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; and Tipredane.

Adrenocortical suppressant: Aminoglutethimide; and Trilostane.

Alcohol deterrent: Disulfiram.

Aldosterone antagonist: Canrenoate Potassium; Canrenone; Dicirenone; Mexrenoate Potassium; Prorenoate Potassium; and Spironolactone.

Amino acid: Alanine; Arginine; Aspartic Acid; Carnitine; Cysteine Hydrochloride; Cystine; Glycine; Histidine; Isoleucine; Leucine; Lysine; Lysine Acetate; Lysine Hydrochloride; Methionine; Phenylalanine; Proline; Serine; Threonine; Tryptophan; Tyrosine; and Valine.

Ammonia detoxicant: Arginine Glutamate; and Arginine Hydrochloride.

Amyotrophic lateral sclerosis agents: Riluzole

Anabolic: Bolandiol Dipropionate; Bolasterone; Boldenone Undecylenate; Bolenol; Bolmantalate; Ethylestrenol; Methenolone Acetate; Methenolone Enanthate; Mibolerone; Nandrolone Cyclotate; Norbolethone; Pizotyline; Quinbolone; Stenbolone Acetate; Tibolone; and Zeranol.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zomepirac Sodium; and Zucapsaicin.

Androgen: Fluoxymesterone; Mesterolone; Methyltestosterone; Nandrolone Decanoate; Nandrolone Phenpropionate; Nisterime Acetate; Oxandrolone; Oxymetholone; Silandrone; Stanozolol; Testosterone; Testosterone Cypionate; Testosterone Enanthate; Testosterone Ketolaurate; Testosterone Phenylacetate; Testosterone Propionate; Trestolone Acetate.

Anesthesia (adjunct to): Sodium Oxybate.

Anesthetic: Aliflurane; Benoxinate Hydrochloride; Benzocaine; Biphenamine Hydrochloride; Bupivacaine Hydrochloride; Butamben; Butamben Picrate; Chloroprocaine Hydrochloride; Cocaine; Cocaine Hydrochloride; Cyclopropane; Desflurane; Dexivacaine; Diamocaine Cyclamate; Dibucaine; Dibucaine Hydrochloride; Dyclonine Hydrochloride; Enflurane; Ether; Ethyl Chloride; Etidocaine; Etoxadrol Hydrochloride; Euprocin Hydrochloride; Fluroxene; Halothane; Isobutamben; Isoflurane; Ketamine Hydrochloride; Levoxadrol Hydrochloride; Lidocaine; Lidocaine Hydrochloride; Mepivacaine Hydrochloride; Methohexital Sodium; Methoxyflurane; Midazolam Hydrochloride; Midazolam Maleate; Minaxolone; Norflurane; Octodrine; Oxethazaine; Phencyclidine Hydrochloride; Pramoxine Hydrochloride; Prilocaine Hydrochloride; Procaine Hydrochloride; Propanidid; Proparacaine Hydrochloride; Propofol; Propoxycaine Hydrochloride; Pyrrocaine; Risocaine; Rodocaine; Roflurane; Salicyl Alcohol; Sevoflurane; Teflurane; Tetracaine; Tetracaine Hydrochloride; Thiamylal; Thiamylal Sodium; Thiopental Sodium; Tiletamine Hydrochloride; and Zolamine Hydrochloride.

Anorectic compound: Dexfenfluramine.

Anorexic agents: Aminorex; Amphecloral; Chlorphentermine Hydrochloride; Clominorex; Clortermine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phemnetrazine Hydrochloride; Phentermine; and Sibutramine Hydrochloride.

Antagonist: Atipamezole; Atosiban; Bosentan; Cimetidine; Cimetidine Hydrochloride; Clentiazem Maleate; Detirelix Acetate; Devazepide; Donetidine; Etintidine Hydrochloride; Famotidine; Fenmetozole Hydrochloride; Flumazenil; Icatibant Acetate; Icotidine; Isradipine; Metiamide; Nadide; Nalmefene; Naloxone Hydrochloride; Naltrexone; Nilvadipine; Oxilorphan; Oxmetidine Hydrochloride; Oxmetidine Mesylate; Quadazocine Mesylate; Ranitidine; Ranitidine Bismuth Citrate; Ranitidine Hydrochloride; Sufotidine; Teludipine Hydrochloride; Tiapamil Hydrochloride; Tiotidine; Vapiprost Hydrochloride; and Zaltidine Hydrochloride.

Anterior pituitary activator: Epimestrol.

Anterior pituitary suppressant: Danazol.

Anthelmintic: Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; Piperazine; Piperazine Citrate; Piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Triclofenol Piperazine; Vincofos; and Zilantel.

Anti-acne: Adapalene; Erythromycin, Salnacedin; and Inocoterone Acetate.

Anti-adrenergic: Acebutolol; Alprenolol Hydrochloride; Atenolol; Bretylium Tosylate; Bunolol Hydrochloride; Carteolol Hydrochloride; Celiprolol Hydrochloride; Cetamolol Hydrochloride; Cicloprolol Hydrochloride; Dexpropranolol Hydrochloride; Diacetolol Hydrochloride; Dihydroergotamine Mesylate; Dilevalol Hydrochloride; Esmolol Hydrochloride; Exaprolol Hydrochloride; Fenspiride Hydrochloride; Flestolol Sulfate; Labetalol Hydrochloride; Levobetaxolol Hydrochloride; Levobunolol Hydrochloride; Metalol Hydrochloride; Metoprolol; Metoprolol Tartrate; Nadolol; Pamatolol Sulfate; Penbutolol Sulfate; Phentolamine Mesylate; Practolol; Propranolol Hydrochloride; Proroxan Hydrochloride; Solypertine Tartrate; Sotalol Hydrochloride; Timolol; Timolol Maleate; Tiprenolol Hydrochloride; Tolamolol; and Zolertine Hydrochloride.

Anti-allergic: Amlexanox; Astemizole; Azelastine Hydrochloride; Eclazolast; Minocromil Nedocromil Nedocromil Calcium; Nedocromil Sodium; Nivimedone Sodium; Pemirolast Potassium Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; and Tixanox.

Anti-amebic: Berythromycin; Bialamicol Hydrochloride; Chloroquine; Chloroquine Hydrochloride; Chloroquine Phosphate; Clamoxyquin Hydrochloride; Clioquinol; Emetine Hydrochloride; Iodoquinol; Paromomycin Sulfate; Quinfamide; Symetine Hydrochloride; Teclozan; Tetracycline; and Tetracycline Hydrochloride.

Anti-androgen: Benorterone; Cioteronel; Cyproterone Acetate; Delmadinone Acetate; Oxendolone; Topterone; and Zanoterone.

Anti-anemic: Epoetin Alfa; Epoetin Beta; Ferrous Sulfate, Dried; and Leucovorin Calcium.

Anti-anginal: Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; and Verapamil Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; and Zalospirone Hydrochloride.

Anti-arthritic: Lodelaben.

Anti-asthmatic: Ablukast; Ablukast Sodium; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Ritolukast; Sulukast; Tiaramide Hydrochloride; Tibenelast Sodium; Tomelukast; Tranilast; Verlukast; and Verofylline Zarirlukast.

Anti-atherosclerotic: Mifobate; and Timefurone.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylate sodium; Aminosalicylic acid; Amoxicillin; Amphomycin; Ampicillin; Ampicillin Sodium; Apalcillin Sodium; Apramycin; Aspartocin; Astromicin Sulfate; A vilamycin; A voparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Betamicin Sulfate; Biapenem; Biniramycin; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftiroxime Pivoxetil; Ceftizoxime Sodium; Ceftriaxone Sodium; Cefuroxime; Cefuroxime Axetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; F osfomycin; F osfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isepamicin; Isoconazole; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifarthiazole; Nifuradene; Nifuraldezone; Nifuratel; Nifuratrone; Nifurdazil; Nifurimide; Nifurpirinol; Nifurquinazol; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-cancer supplementary potentiating agents: Amitryptyline; Amoxapine; Amphotericin B; Antiarrhythmic drugs (e.g., Quinidine); Antihypertensive drugs (e.g., Reserpine); Ca++ antagonists (e.g., Verapamil; Calmodulin inhibitors (e.g., Prenylamine; Caroverine); Citalopram); Clomipramine; Clomipramine); Desipramine; Doxepin; Maprotiline); Nifedipine; Nitrendipine; Non-tricyclic anti-depressant drugs (e.g., Sertraline; Nortriptyline; Protriptyline; Sulfoximine) and Multiple Drug Resistance reducing agents such as Cremaphor EL; Thiol depleters (e.g., Buthionine; Trazodone; Tricyclic anti-depressant drugs (e.g., Imipramine; Trifluoroperazine; Trimipramine; and Triparanol analogues (e.g., Tamoxifen).

Anticholelithic: Monoctanoin.

Anticholelithogenic: Chenodiol; Ursodiol.

Anticholinergic: Alverine Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; and Tropicamide.

Anticoagulant: Ancrod; Ardeparin Sodium; Bivalirudin; Bromindione; Dalteparin Sodium Desirudin; Dicumarol;

Lyapolate Sodium; Nafamostat Mesylate; Phenprocoumon; Tinzaparin Sodium; and Warfarin Sodium.

Anticoccidal: Maduramicin.

Anticonvulsant: Albutoin; Ameltolide; Atolide; Buramate; Cinromide; Citenamide; Clonazepam; Cyheptamide; Dezinamide; Dimethadione; Divalproex Sodium; Eterobarb; Ethosuximide; Ethotoin; Flurazepam Hydrochloride; Fluzinamide; Fosphenytoin Sodium; Gabapentin; Ilepcimide; Lamotrigine; Magnesium Sulfate; Mephenytoin; Mephobarbital; Methetoin; Methsuximide; Milacemide Hydrochloride; Nabazenil; Nafimidone Hydrochloride; Nitrazepam; Phenacemide; Phenobarbital; Phenobarbital Sodium; Phensuximide; Phenytoin; Phenytoin Sodium; Primidone; Progabide; Ralitoline; Remacemide Hydrochloride; Ropizine; Sabeluzole; Stiripentol; Sulthiame; Topiramate; Trimethadione; Valproate Sodium; Valproic Acid; Vigabatrin; Zoniclezole Hydrochloride; and Zonisamide.

Antidepressant: Adinazolam; Adinazolam Mesylate; Alaproclate; Aletamine Hydrochloride; Amedalin Hydrochloride; Amitriptyline Hydrochloride; Aptazapine Maleate; Azaloxan Fumarate; Azepindole; Azipramine Hydrochloride; Bipenamol Hydrochloride; Bupropion Hydrochloride; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pride fine Hydrochloride; Prolintane Hydrochloride; Protriptyline Hydrochloride; Quipazine Maleate; Rolicyprine; Seproxetine Hydrochloride; Sertraline Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine Maleate; Venlafaxine Hydrochloride; Viloxazine Hydrochloride; Zimeldine Hydrochloride; and Zometapine.

Antidiabetic: Acetohexamide; Buformin; Butoxamine Hydrochloride; Camighbose; Chlorpropamide; Ciglitazone; Englitazone Sodium; Etoformin Hydrochloride; Gliamilide; Glibornuride; Glicetanile Sodium; Gliflumide; Glipizide; Glucagon; Glyburide; Glyhexamide; Glymidine Sodium; Glyoctamide; Glyparamide; Insulin; Insulin Human; Insulin Human Zinc; Insulin Human Zinc, Extended; Insulin Human, Isophane; Insulin Lispro; Insulin Zinc; Insulin Zinc, Extended; Insulin Zinc, Prompt; Insulin, Dalanated; Insulin, Isophane; Insulin, Neutral; Linogliride; Linogliride Fumarate; Metformin; Methyl Palmoxirate; Palmoxirate Sodium; Pioglitazone Hydrochloride; Pirogliride Tartrate; Proinsulin Human; Seglitide Acetate; Tolazamide; Tolbutamide; Tolpyrramide; Troglitazone; and Zopolrestat.

Antidiarrheal: Diphenoxylate Hydrochloride; Methylprednisolone; Metronidazole; and Rolgamidine.

Antidiuretic: Argipressin Tannate; Desmopressin Acetate; and Lypressin.

Antidote: Dimercaprol; Edrophonium Chloride; Fomepizole; Levoleucovorin Calcium; Methylene Blue; and Protamine Sulfate.

Antidyskinetic: Selegiline Hydrochloride.

Anti-emetic: Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Flumeridone; Galdansetron Hydrochloride; Granisetron; Granisetron Hydrochloride; Lurosetron Mesylate; Meclizine Hydrochloride; Metoclopramide Hydrochloride; Metopimazine; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; and Zacopride Hydrochloride.

Anti-epileptic: Felbamate; Iamotrigine; Loreclezole; and Tolgabide.

Anti-estrogen: Clometherone; Nafoxidine Hydrochloride; Nitromifene Citrate; Raloxifene Hydrochloride; Tamoxifen Citrate; Toremifene Citrate; and Trioxifene Mesylate.

Antifibrinolytic: Nafamostat Mesylate.

Antifungal: Acrisorcin; Ambruticin; Azaconazole; Azaserine; Basifungin; Bifonazole; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Itraconazole; Kalafungin; Ketoconazole; Lomoftmgin; Lydimycin; Mepartricin; Miconazole; Miconazole Nitrate; Monensin; Monensin Sodium; Naftifine Hydrochloride; Nifuratel Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Pyrrolnitrin; Rutamycin; Sanguinarium Chloride; Saperconazole; Selenium Sulfide; Sinefungin; Sulconazole Nitrate; Terbinafine; Terconazole; Thiram; Tioconazole; Tolciclate; Tolindate; Tolnaftate; Triacetin; Triafungin; Undecylenic Acid; Viridofulvin; Zinc Undecylenate; and Zinoconazole Hydrochloride.

Antiglaucoma agent: Alprenoxime Hydrochloride; Colforsin; Dipivefrin Hydrochloride; Naboctate Hydrochloride; Pilocarpine; and Pirnabine.

Antihemorrhagic: Poliglusam.

Antihemorrheologic: Phentoxifylline.

Antihistaminic: Acrivastine; Antazoline Phosphate; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cirmarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Fexofenadine HCl; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; and Triprolidine Hydrochloride.

Antihyperlipidemic: Cholestyramine Resin; Clofibrate; Colestipol Hydrochloride; Crilvastatin; Dalvastatin; Dextrothyroxine Sodium; Fluvastatin Sodium; Gemfibrozil; Lecimibide; Lovastatin; Niacin; Pravastatin Sodium; Probucol; Simvastatin; Tiqueside; and Xenbucin.

Antihyperlipoproteinemic: Acifran; Beloxamide; Bezafibrate; Boxidine; Cetaben Sodium; Ciprofibrate; Gemcadiol; Halofenate; Lifibrate; Meglutol; Nafenopin; Pimetine Hydrochloride; Theofibrate; Tibric Acid; and Treloxinate.

Antihypertensive: Alfuzosin Hydrochloride; Alipamide; Althiazide; Amiquinsin Hydrochloride; Anaritide Acetate; Atiprosin Maleate; Belfosdil; Bemitradine; Bendacalol Mesylate; Bendroflumethiazide; Benzthiazide; Bethanidine Sulfate; Biclodil Hydrochloride; Bisoprolol; Bisoprolol Fumarate; Bucindolol Hydrochloride; Bupicomide; Buthiazide; Candoxat rilat; Candoxatril; Captopril; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Diltiazem Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancvdine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxvfen Sulfate; Hydralazine Hydrochloride; Hydralazine Polistirex; Hydroflumethiazide; Indacrinone Indapamide; Indolapril Hydrochloride; Indoramin; Indoramin Hydrochloride; Indorenate Hydrochloride; Lacidipine; Leniquinsin; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide Methyclothiazide Methyldopa; Methyldopate Hydrochloride; Metipranolol; Metolazone Metoprolol Fumarate; Metyrosine; Minoxidil; Muzolimine; Nebivolol; Nifidipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; and Zofenoprilat Arginine.

Antihypotensive: Ciclafrine Hydrochloride; and Midodrine Hydrochloride.

Anti-infective: Acyclovir; Difloxacin Hydrochloride; Integrase Inhibitors of HIV and other retroviruses; Lauryl Isoquinolinium Bromide; Moxalactam Disodium; Ornidazole; Pentisomicin; Protease inhibitors of HIV and other retroviruses; and Sarafloxacin Hydrochloride.

Anti-infective (topical): Alcohol; Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofarazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; and Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anitrazafen; Apazone; Balsalazide Disodium; Bendazac; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Difluprednate; Diftalone; Dimethyl Sulfoxide; Drocinonide; Endrysone; Enlimomab; Enolicam Sodium; Etodolac; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Fluocortin Butyl; Fluoromethalone Acetate; Fluquazone; Fluretofen; Fluticasone Propionate; Furaprofen; Furobufen; Halcinonide; Halobetasol Propionate; Halopredone Acetate; Ibuprofen; Ibuprofen Aluminum; Ibuprofen Piconol; Ilonidap; Indomethacin Sodium; Indomethacin; Indoprofen Indoxole; Intrazole; Isoflupredone Acetate; Isoxepac; Isoxicam; Ketoprofen; Lomoxicam; Loteprednol Etabonate; Meclofenamate Sodium; Meclofenamic Acid; Meclorisonc Dibutyrate; Mesalamine; Meseclazone; Methylprednisolone Suleptanate; Morniflumate; Nabumetone; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Pirprofen; Prednazate; Prednisolone Sodium Phosphate; Prifelone; Prodolic Acid; Proquazone; Rimexolone; Romazarit; Salnacedin; Seclazone; Sermetacin; Sudoxicam; Sulindac; Suprofen; Talniflumate; Tenidap; Tenidap Sodium; Tenoxicam; Tesicam; Tesimide; Tixocortol Pivalate; Tolmetin; Tolmetin Sodium; Triclonide; Triflumidate; and Zidometacin.

Antikeratinizinq agent: Doretinel; Linarotene; and Pelretin.

Antimalarial: Amodiaquine Hydrochloride; Amquinate; Artefiene; Chloroquine; Chloroquine Hydrochloride; Cycloguanil Pamoate; Enpiroline Phosphate; Halofantrine Hydrochloride; Hydroxychloroquine Sulfate; Mefloquine Hydrochloride; Menoctone; Primaquine Phosphate; Pyrimethamine; Quinine Sulfate; and Tebuquine.

Antimicrobial: Aztreonam; Chlorhexidine Gluconate; Imidurea; Lycetamine; Nibroxane; Pirazmonam Sodium; Propionic Acid; Pyrithione Sodium; and Tigemonam Dicholine.

Antimigraine: Naratriptan Hydrochloride; Sergolexole Maleate; Sumatriptan Succinate; and Zatosetron Maleate.

Antimitotic: Podofilox.

Antimycotic: Amorolfine.

Antinauseant: Buclizine Hydrochloride; and Cyclizine Lactate.

Antineoplastic: Acivicin; Aclarubicin; Acodazole Hydrochloride; Acronine; Adozelesin; Aldesleukin; Altretamine; Ambomycin; Ametantrone Acetate; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cisplatin; Cladribine; Crisnatol Mesylate; Cyclophosphamide; Cytarabine; Dacarbazine; Dactinomycin; Daunorubicin Hydrochloride; Decitabine; Dexorinaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin, Hydrochloride; Ifosfamide; Ilmofosine; Interferon Alfa-2a; Interferon Alfa-2b; Interferon Alfan3; Interferon Alfa-nI; Interferon Beta-I a; Interferon Gamma-I b; Iproplatin; Irinotecan Hydrochloride; Isotretinoin; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamvcin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Prednimustine; Procarbazine Hydrochloride; Puromycin; Puromycin Hydrochloride; Pyrazofurin; Riboprine; Rogletimide; Safingol Safingol Hydrochloride; Semustine; Simtrazene; Sparfosate Sodium; Sparsomycin; Spiro germanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofarin; Tirapazamine; Topotecan Hydrochloride; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Anti-neoplastic compounds (additional): 20-epi-l,25 Dihydroxyvitamin D3; 5-Ethynyluracil; Abiraterone; Acylfulvene; Adecypenol; ALL-TK Antagonists; Ambamustine; Amidox; Amifostine; Aminolevulinic Acid; Amrubicin; Anagrelide; Andrographolide; Angiogenesis Inhibitors; Antagonist D; Antagonist G; Antarelix; Antiandrogen, Prostatic Carcinoma; Anti-Dorsalizing Morphogenetic Protein-I; Antiestrogen; Antineoplaston; Antisense Oligonucleotides; Aphidicolin Glycinate; Apoptosis Gene Modulators; Apoptosis Regulators; Apurinic Acid; Ara-CDP-DL-PTBA; Arginine Deaminase; Asulacrine; Atamestane; Atrimustine; Axinastatin 1; Axinastatin 2; Axinastatin 3; Azasetron; Azatoxin; Azatyrosine; Baccatin III Derivatives; Balanol; BCR/ABL Antagonists; Benzochlorins; Benzoylstaurosporine; Beta Lactam Derivatives; Beta-Alethine; Betaclamycin B; Betulinic Acid; bFGF Inhibitor; Bisantrene; Bisaziridinylspermine; Bisnafide; Bistratene A; Breflate; Budotitane; Buthionine Sulfoximine; Calcipotriol; Calphostin C; Camptothecin Derivatives; Canarypox IL-2; Capecitabine; Carboxamide-Amino-Triazole; Carboxyamidotriazole; CaRest MI; CARN 700, Cartilage Derived Inhibitor; Casein Kinase Inhibitors (1COS); Castanospermine; Cecropin B; Cetrorelix; Chlorins; Chloroquinoxaline Sulfonamide; Cicaprost; Cis-Porphyrin; Clomifene analogues; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacliximab; Dehydrodidenmin B; Dexifosfamide; Dexverapamil; Didemnin B; Didox; Diethylnorspennine; Dihydro Azacytidine; Dihydrotaxol, 9-; Dioxamycin; Diphenyl Spiromustine; Docosanol; Dolasetron; Doxifluridine; Duocarmycin SA; Ebselen; Ecomustine; Edelfosine; Edrecolomab; Eflomithine; Elemene; Emitefur; Epirubicin; Estramustine Analogue; Estrogen Agonists; Estrogen Antagonists; Exemestane; Fadrozole; Fiezelastine; Flavopiridol; Fluasterone; Fludarabine; Fluorodaunorunicin Hydrochloride; Forfenimex; Formestane; Fostriecin; Fotemustine; Gadolinium Texaphyrin; Gallium Nitrate; Galocitabine; Ganirelix; Gelatinase Inhibitors; Glutathione Inhibitors; Hepsulfam; Heregulin; Hexamethylene Bisacetamide; Hypericin; Ibandronic acid; Idarubicin; Idoxifene; Idramantone; Ilomastat; Imidazoacridones; Immunostimulant Peptides; Insulin-Like Growth Factor-I Receptor Inhibitor; Interferon Agonists; Interferons; Interleukins; Iobenguane; Iododoxorubicin; Ipomeanol, 4-; Irinotecan; Iroplact; Irsogladine; Isobengazole; Isohomohalicondrin B; Itasetron; Jasplakinolide; Kahalalide F; Lamellarin-N Triacetate; Lanreotide; Leinamycin; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lurtotecan; Lutetium Texaphyrin; Lysofylline; Lytic Peptides; Maitansine; Mannostatin A; Marimastat; Maspin; Matrilysin Inhibitors; Matrix Metalloproteinase Inhibitors; Merbarone; Meterelin; Methioninase; Metoclopramide; MIF Inhibitor; Mifepristone; Miltefosine; Mirimostim; Mismatched Double Stranded RNA; Mitoguazone; Mitolactol; Mitomycin analogues; Mitonafide; Mitotoxin Fibroblast Growth Factor-Saporin; Mitoxantrone; Mofarotene; Monoclonal Antibody, Human Chorionic Gonadotrophin; Monophosphoryl Lipid A+Myobacterium Cell Wall Sk; Mopidamol; Multiple Drug Resistance Gene Inhibitor; Multiple Tumor Suppressor I-Based Therapy; Mustard Anticancer Agent; Mycaperoxide B; Mycobacterial Cell Wall Extract; Myriaporone; N-Acetyldinaline; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; N-Substituted Benzamides; 06-Benzylguanine; Okicenone; Oligonucleotides; Onapristone; Ondansetron; Oracin; Oral Cytokine Inducer; Osaterone; Oxaliplatin; Oxaunomycin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentostatin; Pentrozole; Perflubron; Perillyl Alcohol; Phenazinomycin; Phenylacetate; Phosphatase Inhibitors; Picibanil; Pilocarpine Hydrochloride; Pirarubicin; Piritrexim; Placetin A; Placetin B; Plasminogen Activator Inhibitor; Platinum Complex; Platinum Compounds; Platinum-Triamine Complex; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin Polyoxyethylene Conjugate; Raf Antagonists; Raltitrexed; Ramosetron; Ras Famesyl Protein Transferase Inhibitors; Ras Inhibitors; Ras-GAP Inhibitor; Retelliptine Demethylated; Rhenium, Re 186 Etidronate; Rhizoxin; Ribozymes; RII Retinamide; Rohitukine; Romurtide; Roquinimex; Rubiginone B 1; Ruboxyl; Safingol; Saintopin; SarCNU; Sarcophytol A; Sdi 1 Mimetics; Senescence Derived Inhibitor 1; Sense Oligonucleotides; Signal Transduction Inhibitors; Signal Transduction Modulators; Single Chain Antigen Binding Protein; Sizofiran; Sobuzoxane; Sodium Borocaptate; Sodium Phenylacetate; Solverol; Somatomedin Binding Protein; Sonermin; Sparfosic Acid; Spicamycin D; Splenopentin; Spongistatin 1; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Tallimustine; Tamoxifen Methiodide; Tauromustine; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Triacetyluridine; Triciribine; Tropisetron; Turosteride; Tyrosine Kinase Inhibitors; Tyrphostins; UBC Inhibitors; Ubenimex; Urogenital Sinus-Derived Growth Inhibitory Factor; Urokinase Receptor Antagonists; Variolin B; Vector system, Erythrocyte Gene Therapy; Velaresol; Veramine; Verdins; Vinorelbine; Vinxaltine; Vitaxin; Zilascorb; and Zinostatin Stimalamer.

Antineutropenic: Filgrastim; Lenograstim; Molgramostim; Regramostim; and Sargramostim.

Antiobsessional agent: Fluvoxamine Maleate.

Antiparasitic: Abamectin; Clorsulon; and Ivermectin.

Antiparkinsonian: Benztropine Mesylate; Biperiden; Biperiden Hydrochloride; Biperiden Lactate; Carbidopa-Levodopa; Carmantadine; Ciladopa Hydrochloride; Dopamantine; Ethopropazine Hydrochloride; Lazabemide; Levodopa; Lometraline Hydrochloride; Mofegiline Hydrochloride; N axagolide Hydrochloride; Pareptide Sulfate; Procyclidine Hydrochloride; Ropinirole Hydrochloride; and Tolcapone.

Antiperistaltic: Difenoximide Hydrochloride; Difenoxin; Fluperamide; Lidamidine Hydrochloride; Loperamide Hydrochloride; Malethamer; Nufenoxole; Paregoric.

Antipneumocystic: Atovaquone.

Antiproliferative agent: Piritrexim Isethionate.

Antiprostatic hypertrophy: Sitogluside.

Antiprotozoal: Amodiaquine; Azanidazole; Banmidazole; Camidazole; Chlortetracycline Bisulfate Chlortetracycline Hydrochloride; Flubendazole; Flunidazole; Halofuginone Hydrobromide; Imidocarb Hydrochloride; Ipronidazole; Misonidazole; Moxnidazole; Nitarsone; Ronidazole; Sulnidazole; and Tinidazole.

Antipruritic: Methdilazine; Methdilazine Hydrochloride; and Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; and Tepoxalin.

Antipsychotic: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

Antirheumatic: Auranofin; Aurothioglucose; Bindarit; Lobenzarit Sodium; Phenylbutazone; Pirazolac; Prinomide Tromethamine; and Seprilose.

Antischistosomal: Becanthone Hydrochloride; Hycanthone; Lucanthone Hydrochloride; Niridazole; Oxamniquine; Pararosaniline Pamoate; and Teroxalene Hydrochloride.

Antiseborrheic: Chloroxine; Piroctone; Piroctone Olamine; and Resorcinol Monoacetate.

Antisecretory: Arbaprostil; Deprostil; Fenoctimine Sulfate; Octreotide; Octreotide Acetate; Omeprazole Sodium; Rioprostil; Trimoprostil.

Antispasmodic: Stilonium Iodide; Tizanidine Hydrochloride.

Antithrombotic: Anagrelide Hydrochloride; Dalteparin Sodium; Danaparoid Sodium; Dazoxiben Hydrochloride; Efegatran Sulfate; Enoxaparin Sodium; Ifetroban; Ifetroban Sodium; and Trifenagrel.

Antitussive: Benzonatate; Butamirate Citrate; Chlophedianol Hydrochloride; Codeine Polistirex; Codoxime; Dextromethorphan; Dextromethorphan Hydrobromide; Dextromethorphan Polistirex; Ethyl Dibunate; Guaiapate; Hydrocodone Bitartrate; Hydrocodone Polistirex; Levopropoxyphene Napsylate; Noscapine; Pemerid Nitrate; Pipazethate; and Suxemerid Sulfate.

Anti-ulcerative: Aceglutamide Aluminum; Cadexomer Iodine; Cetraxate Hydrochloride; Enisoprost; Isotiquimide; Lansoprazole; Lavoltidine Succinate; Misoprostol; Nizatidine; Nolinium Bromide; Pantoprazole; Pifarnine; Pirenzepine Hydrochloride; Rabeprazole Sodium; Remiprostol; Roxatidine Acetate Hydrochloride; Sucralfate; Sucrosofate Potassium; and Tolimidone.

Anti-urolithic: Cysteamine; Cysteamine Hydrochloride; and Tricitrates.

Antiviral: Acemannan; Acvclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Appetite suppressant: Dexfenfluramine Hydrochloride; Phendimetrazine Tartrate; and Phentermine Hydrochloride.

Benign prostatic hyperplasia therapy agent: Tamsulosin Hydrochloride.

Blood glucose regulators: Acetohexamide and Glipizide; Chloropropamide; and Human insulin.

Bone resorption inhibitor: Alendronate Sodium; Etidronate Disodium; and Pamidronate Disodium.

Bronchodilator: Albuterol; Albuterol Sulfate; Azanator Maleate; Bamifylline Hydrochloride; Bitolterol Mesylate; Butaprost; Carbuterol Hydrochloride; Clorprenaline Hydrochloride; Colterol Mesylate; Doxaprost; Doxofylline; Dyphylline; Enprofylline; Ephedrine; Ephedrine Hydrochloride; Fenoterol; Fenprinast Hydrochloride; Guaithylline; Hexoprenaline Sulfate; Hoquizil Hydrochloride; Ipratropium Bromide; Isoetharine; Isoetharine Hydrochloride; Isoetharine Mesylate; Isoproterenol Hydrochloride; Isoproterenol Sulfate; Metaproterenol Polistirex; Metaproterenol Sulfate; Nisbuterol Mesylate; Oxtriphylline; Picumeterol Fumarate; Piquizil Hydrochloride; Pirbuterol Acetate; Pirbuterol Hydrochloride; Procaterol Hydrochloride; Pseudoephedrine Sulfate; Quazodine; Quinterenol Sulfate; Racepinephrine; Racepinephrine Hydrochloride; Reproterol Hydrochloride; Rimiterol Hydrobromide; Salmeterol; Salmeterol Xinafoate; Soterenol Hydrochloride; Sulfonterol Hydrochloride; Suloxifen Oxalate; Terbutaline Sulfate; Theophylline; Xanoxate Sodium; Zindotrine; and Zinterol Hydrochloride.

Carbonic anhydrase inhibitor: Acetazolamide; Acetazolamide Sodium; Dichlorophenamide; Dorzolamide Hydrochloride; Methazolamide; and Sezolamide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; and Transcainide.

Cardioprotectant: Dexrazoxane; and Draflazine.

Cardiotonic agent: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; and Vesnarinone.

Cardiovascular agent: Dopexamine; and Dopexamine Hydrochloride.

Cerebral ischemia agent: Dextrorphan Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostiamine Methylsulfate; Neostigmine Bromide; Physostigmine; Physostigmine Salicylate; Physostigmine Sulfate; Pilocarpine Nitrate; and Pyridostigmine Bromide.

Cholinergic agonist: Xanomeline; and Xanomeline Tartrate.

Cholinesterase Deactivator: Obidoxime Chloride; Pralidoxime Chloride; Pralidoxime Iodide; and Pralidoxime Mesylate.

Coccidiostat: Arprinocid; Narasin; Semduramicin; and Semduramicin Sodium.

Cognition adjuvant: Ergoloid Mesylates; Piracetam; Pramiracetam Hydrochloride; Pramiracetam Sulfate; and Tacrine Hydrochloride.

Cognition enhancer: Besipirdine Hydrochloride; Linopirdine; and Sibopirdine.

Contrast Media: Barium Sulfate; Diatrizoate Sodium; Erythrosine Sodium; Iopanoic Acid; Ipodate Calcium; Metyrapone; and Tyropanoate Sodium.

Diagnostic aid: Aminohippurate Sodium; Anazolene Sodium; Arclofenin; Bentiromide; Benzylpenicilloyl Polylysine; Butedronate Tetrasodium; Butilfenin; Coccidioidin; Corticorelin Ovine Triflutate; Corticotropin Zinc Hydroxide; Corticotropin, Repository; Diatrizoate Meglumine; Diatrizoic Acid; Diphtheria Toxin for Schick Test; Disofenin; Ethiodized Oil; Etifenin; Exametazime; Ferristenc; Ferumoxides; Ferumoxsil; Fluorescein; Fluorescein Sodium; Gadobenate Dimeglumine; Gadodiamide; Gadopentetate Dimegiumine; Gadoteridol; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopentol; Iophendylate; Ioprocemic Acid; Iopronic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxagiate Sodium; Ioxaglate Meglumine; Ioxaglic Acid; Ioxilan; Ioxotrizoic Acid; Ipodate Sodium; Iprofenin; Isosulfan Blue; Leukocyte Typing Serum; Lidofenin; Mebrofenin; Meglumine; Metrizamide; Metrizoate Sodium; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; and Xylose.

Diuretic: Ambuphylline; Ambuside; Amiloride Hydrochloride; Azolimine; Azosemide; Brocrinat; Bumetanide; Chlorothiazide; Chlorthalidone; Clazolimine; Clorexolone; Ethacrynate Sodium; Ethacrynic Acid; Etozolin; Fenquizone; Furosemide; Hydrochlorothiazide; Isosorbide; Mannitol Mefruside; Ozolinone; Piretanide; Spiroxasone; Torsemide; Triamterene; Triflocin; and Urea.

Dopaminergic agent: Ibopamine.

Ectoparasiticide: Nifluridide; Permethrin.

Emetic: Apomorphine Hydrochloride.

Enzyme inhibitor: 30 Polignate Sodium; Acetohydroxamic Acid; Alrestatin Sodium; Aprotinin; Benazepril Hydrochloride; Benazeprilat; Benurestat; Bromocriptine; Bromocriptine Mesylate; Cilastatin Sodium; Flurofamide; Lergotrile; Lergotrile Mesylate; Levcycloserine; Libenzapril; Pentopril; Pepstatin; Perindopril; Sodium Amylosulfate; Sorbinil; Spirapril Hydrochloride; Spiraprilat; Taleranol; Teprotide; Tolfamide; and Zofenopril Calcium.

Estrogen: Chlorotrianisene; Dienestrol; Diethylstilbestrol; Diethylstilbestrol Diphosphate; Equilin; Estradiol; Estradiol Cypionate; Estradiol Enanthate; Estradiol Undecylate; Estradiol Valerate; Estrazinol Hydrobromide; Estriol; Estrofurate; Estrogens, Conjugated; Estrogens, Esterified; Estrone; Estropipate; Ethinyl Estradiol; Fenestrel; Mestranol; Nylestriol; and Quinestrol.

Fibrinolytic: Anistreplase; Bisobrin Lactate; and Brinolase.

Free oxygen radical scavenger: Pegorgotein.

Gastric Acid Suppressant: Lansoprazole, Pantoprazole and Omeprazole.

Gastrointestinal Motility agents: Cisapride.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; and Triamcinolone Hexacetonide.

Gonad-stimulating principle: Buserelin Acetate; Clomiphene Citrate; Ganirelix Acetate; Gonadorelin Acetate; Gonadorelin Hydrochloride; Gonadotropin, Chorionic; and Menotropins.

Hormone: 17 Alpha Dihydroequilenin; 17 Alpha Dihydroequilin; 17 Alpha Estradiol; 17 Beta Estradiol; 17 Hydroxy Progesterone; Androstenedione; Clomiphene; Cosyntropin; Dehydroepiandrosterone; Dihydroestosterone; Equilenin; Ethyndiol; Follicle Regulatory Protein; Follicle Stimulating Hormone; Folliculostatin; Gonadoctrinins; Gonadorelin; Gonadotropins; Han Memopausal Gonadotropins; Human Chorionic Gonadotropin; Insulin Growth Factor; Leuprolide; Levonorgestrel; Luteinizing hormone; Luteinizing Hormone Releasing Hormone and Analogs; Medroxyprogesterone; Megestrol; Metogest; Norethindrone; Norethynodrel; Norgestrel; Oocyte Maturation Inhibitor; Oxytocin; Pituitary, Posterior; Progesterone; Relaxin; Seractide Acetate; Somalapor; Somatrem; Somatropin; Somenopor; Somidobove; Tamoxifen; Urofollitropin; and Vasopressin.

Hypocholesterolemic: Lifibrol.

Hypoglycemic: Darglitazone Sodium; and Glimepiride.

Hypolipidemic: Azalanstat Dihydrochloride; Colestolone; Surfomer; and Xenalipin.

Hypotensive: Viprostol.

Immunizing agent: Antirabies Serum; Antivenin; Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; Rho(D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Vaccinia Immune Globulin; VaricellaZoster Immune Globulin; and Yellow Fever vaccine.

Immunomodulator: Dimepranol Acedoben; Imiquimod; Interferon Beta-Ib; Lisofylline; Mycophenolate Mofetil; and Przatide Copper Acetate.

Immunorequlator: Azarole; Fanetizole Mesylate; Frentizole; Oxamisole Hydrochloride; Ristianol Phosphate; Thymopentin; and Tilomisole.

Immunostimulant: Loxoribine; and Teceleukin.

Immunosuppressant: Azathioprine; Azathioprine Sodium; Cyclosporine; Daltroban; Gusperimus Trihydrochloride; Sirolimus; Tacrolimus.

Impotence therapy adjunct: Delequamine Hydrochloride.

Inhibitor: Acarbose; Atorvastatin Calcium; Benserazide; Brocresine; Carbidopa; Clavulanate Potassium; Dazmegrel; Docebenone; Epoprostenol; Epoprostenol Sodium; Epristeride; Finasteride; Flurbiprofen Sodium; Furegrelate Sodium; Lufironil; Miglitol; Orlistat; Pimagedine Hydrochloride; Pirmagrel; Ponalrestat; Ridogrel; Sulbactam Benzathine; Sulbactam Pivoxil; Sulbactam Sodium; Suronacrine Maleate; Tazobactam; Tazobactam Sodium; Ticlopidine Hydrochloride; Tirilazad Mesylate; Tolrestat; Velnacrine Maleate; Zifrosilone; and Zileuton.

Keratolytic: Alcloxa; Aldioxa; Dibenzothiophene; Etarotene; Motretinide-I Picotrin Diolamine; Salicylic Acid; Sumarotene; Tazarotene; Tetroquinone; and Tretinoin.

LHRH agonist: Deslorelin; Goserelin; Histrelin; Lutrelin Acetate; and Nafarelin Acetate.

Liver disorder treatment: Malotilate.

Luteolysin: Fenprostalene.

Memory adjuvant: Dimoxamine Hydrochloride; and Ribaminol.

Mental performance enhancer: Aniracetam.

Mood regulator: Fengabine.

Mucolytic: Acetylcysteine; Carbocysteine; and Domiodol.

Mucosal Protective agents: Misoprostol (Cytotec).

Mydriatic: Berefrine.

Nasal decongestant: Nemazoline Hydrochloride; Pseudoephedrine Polistirex.

Neuroleptic: Duoperone Fumarate; and Risperidone.

Neuromuscular blocking agent: Atracurium Besylate; Cisatracurium Besylate; Doxacurium Chloride; Gallamine Triethiodide; Metocurine Iodide; Mivacurium Chloride; Pancuronium Bromide; Pipecuronium Bromide; Rocuronium Bromide; Succinylcholine Chloride; Tubocurarine Chloride; and Vecuronium Bromide.

Neuroprotective: Dizocilpine Maleate.

NMDA antagonist: Selfotel.

Non-hormonal sterol derivative: Pregnenolone Succinate.

Oxytocic: Carboprost; Carboprost Methyl; Carboprost Tromethamine; Dinoprost; Dinoprost Tromethamine; Dinoprostone; Ergonovine Maleate; Metenoprost; Methylergonovine Maleate; and Sparteine Sulfate.

Paget's disease agents: Tiludronate Disodium.

Progestin: Algestone Acetophenide; Amadinone Acetate; Anagestone Acetate; Chlormadinone Acetate; Cingestol; Clogestone Acetate; Clomegestone Acetate; Desogestrel; Dimethisterone; Dydrogesterone; Ethynerone; Ethynodiol Diacetate; Etonogestrel; Flurogestone Acetate; Gestaclone; Gestodene; Gestonorone Caproate; Gestrinone; Haloprogesterone; Hydroxyprogesterone Caproate; Lynestrenol; Medrogestone; Med roxyprogesterone Acetate; Methynodiol Diacetate; Norethindrone Acetate; Norgestimate; Norgestomet; Oxogestone Phenpropionate; Quingestanol Acetate; Quingestrone; and Tigestol.

Prostaglandin: Cloprostenol Sodium; Fluprostenol Sodium; Gemeprost; Prostalene; and Sulprostone.

Prostate growth inhibitor: Pentomone.

Prothyrotropin: Protirelin.

Psychotropic: Minaprine.

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine 1131; Tolpovidone 1131; Triolein 1125; and Triolein 1131.

Regulator: Calcifediol; Calcitonin; Calcitriol; Clodronic Acid; Dihydrotachysterol; Etidronic Acid; Oxidronic Acid; Piridronate Sodium; Risedronate Sodium; and Secalciferol.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalamide; Fenyripol Hydrochloride; Fetoxylate Hydrochloride; Flavoxate Hydrochloride; Fletazepam; Flumetramide; Hexafluorenium Bromide; Isomylamine Hydrochloride; Lorbamate; Mebeverine Hydrochloride; Mesuprine Hydrochloride; Metaxalone; Methixene Hydrochloride; Methocarbamol; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; and Xilobam.

Repartitioninq agent: Cimaterol.

Scabicide: Amitraz; Crotamiton.

Sclerosing agent: Ethanolamine Oleate; Morrhuate Sodium; Tribenoside.

Sedative: Propiomazine.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam Ethchlorvynol; Etomidate; Fenobam; Flunitrazepam; Fosazepam; Glutethimide; Halazepam; Lon-netazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Tracazolate; Trepipam Maleate; Triazolam; Tricetamide; Triclofos Sodium; Trimetozine; Uldazepam; Zaleplon; Zolazepam Hydrochloride; and Zolpidem Tartrate.

Selective adenosine A1 antagonist: Apaxifylline.

Serotonin antagonist: Altanserin Tartrate; Amesergide; Ketanserin; and Ritanserin.

Serotonin inhibitor: Cinanserin Hydrochloride; Fenclonine; Fonazine Mesylate; and Xylamidine Tosylate.

Serotonin receptor antagonist: Tropanserin Hydrochloride.

Steroid: Dexamethasone Acefurate; and Mometasone Furoate.

Stimulant: Amfonelic Acid; Amphetamine Sulfate; Ampyzine Sulfate; Arbutamine Hydrochloride; Azabon; Caffeine; Ceruletide; Ceruletide Diethylamine; Dazopride Fumarate; Dextroamphetamine; Dextroamphetamine Sulfate; Difluanine Hydrochloride; Dimefline Hydrochloride; Doxapram Hydrochloride; Ethamivan; Etryptamine Acetate; Fenethylline Hydrochloride; Flubanilate Hydrochloride; Flurothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; and Xamoterol Fumarate.

Suppressant: Amflutizole; Colchicine; Tazofelone.

Symptomatic multiple sclerosis: Fampridine.

Synergist Proadifen Hydrochloride.

Thyroid hormone: Levothyroxine Sodium; Liothyronine Sodium; and Liotrix.

Thyroid inhibitor: Methimazole; and Propylthiouracil.

Thyromimetic: Thyromedan Hydrochloride.

Tranquilizer: Bromazepam; Buspirone Hydrochloride; Chlordiazepoxide; Clazolam; Clobazam; Clorazepate Dipotassium; Clorazepate Monopotassium; Demoxepam; Dexmedetomidine; Enciprazine Hydrochloride; Gepirone Hydrochloride; Hydroxyphenamate; Hydroxyzine Hydrochloride; Hydroxyzine Pamoate; Ketazolam; Lorazepam; Lorzafone; Loxapine; Loxapine Succinate; Medazepam Hydrochloride; Nabilone; Nisobamate; Oxazepam; Pentabamate; Pirenperone; Ripazepam; Rolipram; Sulazepam; Taciamine Hydrochloride; Temazepam; Triflubazam; Tybamate; and Valnoctamide.

Unstable angina agents: Tirofiban Hydrochloride.

Uricosuric: Benzbromarone; Irtemazole; Probenecid; Sulfinpyrazone.

Vasoconstrictor: Angiotensin Amide; Felypressin; Methysergide; and Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; and Xanthinol Niacinate.

Wound healing agent: Ersofermin.

Xanthine oxidase inhibitor: Allopurinol; and Oxypurinol.

Other active agents include: 16-Alpha Fluoroestradiol; 16Alpha-Gitoxin; 16-Eplestriol; 17 Alpha Estradiol; 17Beta Estradiol; IAlpha-Hydroxyvitamin D2; 1-Decpyrrolidinone; 1-Dodecpyrrolidinone; 22-Oxacalcitriol; 2CVV; 2'-Nor-cGMP; 3-Isobutyl GABA; 6-FUDCA; 7-Methoxytacrine; Abacavir Sulfate; Abanoquil; Abecarnil; Acadesine; Acamprosate; Acebutolol Hydrochloride; Aceclofenac; Acetomepregenol; Acetrizoate Sodium; Acetylcysteine, N—; Acetyldigitoxin; Acetyl-L-carnitine; Acetylmethadol; Acipimox; Acitemate; Aclatonium; Aconiazide; Acrivastinet; Adafenoxate; Adatanserin; Adefovir Dipivoxil; Adelmidrol; Ademetionine; Adiposin; Adrafinil; Alacepril; Aladapcin; Alaptide; Alatrofloxacin Mesylate; Albolabrin; Albumin Chromated Cr-51 Serum; Albumin Human; Albumin Iodinated I-125 Serum; Albumin Iodinated 1-131 Serum; Aldecalmycin; Alendronic Acid; Alentemol; Alfacalcidol; Alfuzosin; Alglucerase; Alinastine; Alitretinoin; Alkavervir; Allopurinol Sodium; Almotriptan Malate; Alosetron; Alpha Idosone; Alpha-Tocopherol; Alpha-Tocopherol Acetate; Alseroxylon; Altromycin B; Amantadine-HCl; Ambenonium Chloride; Amelometasone; Amezinium Metilsulfate; Amfebutamone; Amifloxacin; Aminolevulinic Acid Hydrochloride; Aminosalicylic Acid Resin Complex; Amiodarone Hydrochloride; Amisulpride; Amlodipine; Ammonium Lactate; Amphetamine Adipate; Amphetamine Aspartate; Amphetamine Resin Complex; Ampiroxicam; Amprenavir; Amylin; Amythiamicin; Ananain; Anaritide; Anileridine Phosphate; Anisindione; Anordrin; Apadoline; Apafant; Apraclonidine; Aprepitant; Aprosulate Sodium; Aprotinin Bovine; Aptiganel; Aranidipine; Arbekacin; Arbidol; Arbutamine; Arecatannin B 1; Argatroban; Aripiprazol; Aripiprazole; Arotinolol; Articaine Hydrochloride; Ascorbic Acid; Asimadoline; Aspalatone; Asperfuran; Aspoxicillin; Atazanavir Sulfate; Atenolol, S—; Atevirdine; Atomoxetine Hydrochloride; Atpenin B; Atrinositol; Aureobasidin A; Avobenzone; Azadirachtine; Azelaic Acid; Azelastine; Azelnidipine; Azimilide; Azithromycin Dihydrate; Aztreonwn; Baccatin III; Bacoside A; Bacoside B; Bactobolamine; Balazipone; Balhimycin; Balofloxacin; Balsalazide; Bambuterol; Baohuoside 1; Barnidipine; Batebulast; Beauvericin; Becaplermin; Becliconazole; Beclomethasone Dipropionate Monohydrate; Befloxatone; Bellenamine; Benflumetol; Benidipine; Bentoquatam; Benzisoxazole; Benzoidazoxan; Benzoyl Peroxide; Benzphetamine Hydrochloride; Benzquinamide Hydrochloride; Benztropine; Benzyl Benzoate; Benzyl Penicilloyl-Polylysine; Bepridil; Beractant; Beraprost; Berlafenone; Bertosamil; Besipirdine; Beta-Carotene; Betaine, Anhydrous; Betamipron; Betaxolol; Betazole Hydrochloride; Bevantolol; Bexarotene; Bifemelane; Bimakalim; Bimatoprost; Bimithil; Binospirone; Biotin; Bioxalomycin Alpha2; Biriperone; Bisaramil; Bisaziridinylspermine; Bis-Benzimidazole A; Bis-Benzimidazole B; Bismuth Subsalicylate; Bistramide D; Bistramide K; Boldine; Bopindolol; Bortezomib; Brefeldin; Brimonidine; Brinzolamide; Bromfenac; Bucindolol; Budipine; Bunazosin; Butenafine; Butenafine Hydrochloride; Butixocort Propionate; Cabergoline; Caffeine Citrate; Calanolide A; Calcitonin Human; Calcitonin, Salmon; Calcium; Calcium Acetate; Calcium Gluceptate; Calcium Metrizoate; Calfactant; Camonagrel; Candesartan; Candesartan Cilexetil; Candoxatrilat; Capromab; Capsaicin; Carbarnazepine; Carbazomycin C; Carbetocin; Carbidopa/Levodopa; Carbovir; Carboxymethylated Beta-I,3-Glucan; Carperitide; Carteolol; Carumonam; Carvotroline; Caspofungin Acetate; Cebaracetam; CefadroxillCefadroxil Hemihydrate; Cefcapene Pivoxil; Cefdaloxime Pentexil Tosilate; Cefditoren Pivoxil; Cefepime Hydrochloride (Arginine Formulation); Cefetamet; Cefetamet Pivoxil; Cefffietazole; Cefluprenam; Cefminox; Cefodizime; Cefoselis; Cefotiam; Cefotiam Hexetil; Cefozopran; Cefpirome; Cefsulodin; Ceftazidime (Arginine Formulation); Ceftazidime Sodium; Cefteram; Ceftibuten Dihydrate; Ceftriaxone; Celastrol; Celecoxib; Celikalim; Celiprolol; Cellulose Sodium Phosphate; Cepacidine A; Cericlamine; Cerivastatin; Cerivastatin Sodium; Certoparin Sodium; Cetiedil; Cetirizine; Cetyl Alcohol; Cevimeline Hydrochloride; Chlormerodrin, Hg-197; Chlormezanone; Chloroorienticin A; Chloroorienticin B; Cholecalciferol; Cholestyramine; Choriogonadotropin Alfa; Chromic Phosphate, P-32; Chymopapain; Chymotrypsin; Cibenzoline; Ciclesonide; Cicloprolol; Cilansetron; Cilnidipine; Cilobradine; Cilostazol; Cimetropiurn Bromide; Cinitapride; Cinolazepam; Ciprostene; Cisapride Monohydrate; Cisatracurium, Besilate; Cistinexine; Citalopram; Citalopram Hydrobromide; Citicoline; Citreamicin Alpha; Clausenamide; Clidinium Bromide; Clinafloxacin; Clomethiazole; Clopidogrel; Clopidogrel Bisulfate; Cobalt Chloride, Co-57; Cobalt Chloride, Co-60; Colesevelam Hydrochloride; Colestimide; Colfosceril Palmitate; Complestatin; Contignasterol; Contortrostatin; CorticotropinZinc Hydroxide; Cosalane; Costatolide; Cotinine; Cournermycin AI; Cryptenamine Acetates; Cryptenamine Tannates; Cucumariosid; Curdlan Sulfate; Curiosin; Cyanocobalamin; Cyanocobalamin, Co-57; Cyanocobalamin, Co-58; Cyanocobalamin, Co-60; Cyclazosin; Cyclic HPMPC; Cyclobenzaprine; Cyclobut A; Cyclobut G; Cyclocapron; Cyclosin; Cyclothialidine; Cyclothiazomycin; Cycrimine Hydrochloride; Cyproterone; Cysteamine Bitartrate; Cytochalasin B; Dactimicin; Daidzein; Daidzin; Danaparoid; Daphnodorin A; Dapiprazole; Dapitant; Darifenacin; Darlucin A; Darsidomine; Daunorubicin Citrate; DdUTP; Decamethonium Bromide;

Deferiprone; Deferoxamine Mesylate; Dehydrodidemnin B; Delapril; Delequarnine; Delfaprazine; Delmopinol; Delphinidin; Deoxypyridinoline; Deprodone; Depsidomycinderamciclane; Dermatan Sulfate; Deserpidine; Desirudin; Desloratadine; Desmopressin; Desoxoamiodarone; Desoxyribonuclease; Detajrnium Bitartrate; Dexketoprofen; Dexloxiglumide; Dexmethylphenidate Hydrochloride; Dexrazoxane Hydrochloride; Dexsotalol; Dextrin 2-Sulphate; Dextroamphetamine Adipate; Dextroamphetamine Resin Complex; Dextroamphetamine Saccharate; Dextrose; Diclofenac Digolil; Dicranin; Dienogest; Diethylhomospennine; Diethylnorspermine; Difenoxin Hydrochloride; Dihydrexidine; Diltiazeim; Dimethyl Prostaglandin Al; Dimethylhomospermine; Dimiracetarn; Dimyristoyl Lecithin; Diphemanil Methylsulfate; Diphencyprone; Diphenylpyraline Hydrochloride; Diprafenone; Dipropylnorspermine; Discodermolide; Divalproex; Docarparnine; Docosanol, 1-; Dolasetron Mesylate Monohydrate; Domitroban; Donepezil Hydrochloride; Dorzolamide; Dosmalfate; Dotarizine; Doxazosin; Doxercalciferol; Draculin; Drosperidone; Drospirenone; Drotaverine Acephyllinate; Droxicam; Dutasteride; Ebiratide; Ebrotidine; Ecabapide; Ecabet; Ecdisteron; Echicetin; Echistatin; Ecteinascidin 722; Ecteinascidin 729; Ecteinascidin 743; Edaravone; Edetate Calcium Disodium; Edetate Disodium; Edobacomab; Edrecolornab; Efavirenz; Efegatran; Efonidipine; Egualen; Elcatonin; Eletriptan; Eletriptan Hydrobromide; Elgodipine; Eliprodil; Eltenac; Emakalim; Emedastine; Emedastine Difumarate; Emiglitate; Emoctakin; Emtricitabine; Enalapril; Enazadrem; Enfuvirtide; Englitazone; Entacapone; Enterostatin; Eplerenone; Epoxymexrenone; Eptastigmine; Eptifibatide; Erdosteine; Ergocalciferol; Ersentilide; Ertapenem Sodium; Erythritol; Escitalopram Oxalate; Esomeprazole Magnesium; Estazolam; Estradiol Acetate; Esuprone; Etanterol; Ethacizin; Ethchlorvynol; Ethinamate; Ethinylestradiol; Ethoxzolamide; Etidocaine Hydrochloride; Etizolam; Etrabamine; Eveminomicin; Examorelin; Ezetimibe; Faerieftmgin; Fantofarone; Famciclovir; Faropenem; Fasidotril; Fasudil; Fedotozine; Felbarnate; Fenofibrate; Fenoldopam; Fenspiride; Fentanyl; Fenticonazole; Fepradinol; Ferpifosate Sodium; Ferristene; Ferrixan; Ferrous Citrate, Fe-59; Fexofenadine Hydrochloride; Fibrinogen, 1-125; Fibrinolysin; Flecainide; Flerobuterol; Flesinoxan; Flezelastine; Flobufen; Flomoxef; Florfenicol; Florifenine; Flornastat; Flosatidil; Fludeoxyglucose, F-18; Flumecinol; Flunarizine; Fluocalcitriol; Fluoxetine, R—; Fluoxetine, S—; Fluparoxan; Flupirtine; Flurbiprofen Axetil; Flurithromycin; Flutamide; Flutrimazole; Fluvastatin; Fluvoxamine; Folic Acid; Follitropin Alfa; Follitropin Alfa/Beta; Fomivirsen Sodium; Fondaparinux Sodium; Forasartan; Formoterol; Formoterol Fumarate; Formoterol, R,R; Fosinopril; Fosphenytoin; Frovatriptan Succinate; Fulvestrant; Furosernide; Gadobenic Acid; Gadobutrol; Gadodiamide-EOB-DTPA; Gadopentetate Dimeglumine; Gadoteric Acid; Galantamine; Galantamine Hydrobromide; Galdansetron; Gallopamil; Gamolenic Acid; Gatifloxacin; Gefitinib; Gemifloxacin Mesylate; Gemtuzumab Ozogamicin; Gepirone; Girisopam; Glaspimod; Glatiramer Acetate; Glaucocalyxin A; Glucagon Hydrochloride; Glucagon Hydrochloride Recombinant; Glucagon Recombinant; Gluconolactone; Glutapyrone; Glutathione Disulfide; Glycopine; Glycopril; Goserelin Acetate; Grepafloxacin; Grepafloxacin Hydrochloride; Guaifenesin; Guanidine Hydrochloride; Halichondrin B; Halofantrine; Halomon; Haloperidol Lactate; Halopredone; Hatomarubigin C; Hatornambigin D; Hatornamicin; Hatornarubigin A; Hatornarubigin B; Heparin Calcium; Heparin Sodium; Hexocyclium Methylsulfate; Hexylcaine Hydrochloride; Histrelin Acetate; Hyaluronidase; Hydrocortamate Hydrochloride; Hydrocortisone Cypionate; Hydrocortisone Probutate; Hydro quinone; Hydroxocobalamin; Hydroxypropyl Cellulose; Hydroxystilbamidine Isethionate; Ibandronate Sodium; Ibogaine; Ibudilast; Ibuprofen Potassium; Icodextrin; Illimaquinone; Iloprost; Imatinib Mesylate; Imidapril; Imidazenil; Imiglucerase; Imipramine Pamoate; Inamrinone Lactate; Indapamide; Indinavir; Indinavir Sulfate; Indium In-III Oxyquinoline; Indium In-III Pentetate Disodium; Indium In-III Pentetreotide Kit; Indometacin; Indometacin Farnesil; Indomethacin Sodium; Inocoterone; Inogatran; Inolimomab; Insulin Aspart; Insulin Aspart Protamine; Insulin Glargine; Insulin Lispro Protamine; Interferon Alfa; Interferon Alfa-NI; Interferon Beta; Interferon Beta-IaI; Interferon Gamma-I A; Interferon Gamma-I B; Interferon Omega; Interferon, Consensus; Interleukin-3; Interleukin-1; Interleukin-I Beta; Interleukin-10; Interleukin-II; Interleukin-12; Interleukin-15; Interleukin-2; Interleukin-4; Interleukin-5; Interleukin-7; Interleukin-8; InterleukinI Alpha; Intrinsic Factor; Inulin; Invert Sugar; Iobenguane Sulfate I 131; Iobitridol; Iodamide Meglumine; Iodipamide Sodium; Iodoamiloride; Iodohippurate Sodium, 1-123; Iodohippurate Sodium, 1-131; Iofetamine Hydrochloride 1-123; Iofratol; Iopromide; Iopyrol; Iorneprol; Iothalamate Sodium, 1-125; Iotriside; Ioxaglate Sodium; Ipazilide; Ipenoxazone; Ipidacrine; Ipomeanol, 4; Ipriflavone; Ipsapirone; Irbesartan; Irloxacin; Iron Dextran; Iron Sucrose; Irternazole; Isalsteine; Isbogrel; Iseparnicin; Isofloxythepin; Isopropyl Unoprostone; Itameline; Itopride; Ketoprofen, R—; Ketoprofen, S—; Ketorolac; Lactitol; Lactivicin; Lactulose; Laennec; Lafutidine; Lanoconazole; Lanperisone; Larnifiban; Larnotrigine; Latanoprost; Lateritin; Laurocaprarn; Leflunomide; Lemefloxacin; Leminoprazole; Lenercept; Lepirudin; Leptin; Lercanidipine; Lerisetron; Lernildipine; Lesopitron; Letrazuril; Leucomyzin; Levalbuterol Hydrochloride; Levallorphan Tartrate; Levamisole Hydrochloride; Levetiracetam; Levobetaxolol; Levobunolol; Levobupivacaine; Levobupivacaine Hydrochloride; Levocabastine; Levocarnitine; Levodropropizine; Levofloxacin; Levopropoxyphene Napsylate, Anhydrous; Levormeloxifene; Levornoprolol; Levosimendan; Levosulpiride; Lindane; Linezolid; Linotroban; Linsidornine; Lintitript; Lintopride; Lipase; Lirexapride; Lithium Carbonate; Lithium Citrate; Lodoxamide; Lomerizine; Lonazolac; Lopinavir; Lorglumide; Losartan; Losigamone; Loteprednol; Loviride; Loxapine Hydrochloride; LpdR; Lubeluzole; Lutetium; Luzindole; Lydicamycin; Lysostaphin; Magainin 2 Arnide; Magnesium Acetate; Magnesium Acetate Tetrahydrate; Magnolol; Malathion; Mallotochromene; Mallotojaponin; Mangafodipir; Mangafodipir Trisodium; Manidipine; Maniwamycin A; Mannitol; Manurnycin E; Manurnycin F; Mapinastine; Martek 8708; Martek 92211; Massetolide; Meglumine Metrizoate; Meloxicam; Melphalan Hydrochloride; Menadiol Sodium Diphosphate; Menadione; Meprednisone; Mequinol; Mersalyl Sodium; Mesna; Metformin Hydrochloride; Methantheline Bromide; Metharbital; Methoxamine Hydrochloride; Methoxatone; Methoxsalen; Methscopolamine Bromide; Methyclothiazide; Methyldopa; Methylhistamine, R-alpha; Methylinosine Monophosphate; Methylprednisolone Aceponate; Methyprylon; Metiparnide; Metipranolol Hydrochloride; Metolazone; Metoprolol Fumarate; Metoprolol, S—; Metoprotol Tartrate; Metrifonate; Metrizoate Magnesium; Metrizoic Acid; Mezlocillin Sodium Monohydrate; Michellarnine B; Microcolin A; Midodrine; Miglustat; Milacernide; Milarneline; Mildronate; Milnacipran; Milrinone Lactate; Miokarnycin; Mipragoside; Mirfentanil; Mivazerol; Mixanpril; Mizolastine; Mizoribine; Moexipril; Moexipril Hydrochloride; Mofezolac; Mometasone; Mometasone Furoate Monohydrate; Monobenzone; Montirelin; Moracizine; Moricizine Hydrochloride; Mosapramine; Mosapride; Motilide; Moxifloxacin Hydrochloride; Moxiraprine; Moxonidine; Mupirocin; Mupirocin Calcium; Mycophenolate Mofetil Hydrochloride; Nadifloxacin; Nadroparin Calcium; Nafadotride; Nafamostat; Naftopidil; Naglivan; Nalmefene Hydrochloride; Naltrexone Hydrochloride; Napadisilate; Napsagatran; Naratriptan; Nasaruplase; Nateglinide; Nateplasel; Nelfinavir Mesylate; Nesiritide; Niacinamide; Nicotine; Nicotine Polacrilex; Niperotidine; Niravoline; Nisin; Nitazoxanide; Nitecapone; Nitisinone; Nitrendipine, S—; Nitrofurantoin Monohydrate; Nitrofurantoin Sodium; Nitrofurantoin, Macrocrystalline; Nitrofurazone; Nitroglycerin; Nonoxynol-9; Norelgestromin; Octyl Methoxycinnamate; Olmesartan Medoxomil; Olopatadine; Olopatadine Hydrochloride; Olprinone; Olsalazine; Omeprazole Magnesium; Ondansetron, R—; Oral Hypoglyceremics; Orphenadrine Hydrochloride; Oseltamivir Phosphate; Otenzepad; Oxamisole; Oxaprozin Potassium; Oxcarbazepine; Oxiconazole; Oxiracetam; Oxodipine; Oxybenzone; Oxybutynin; Oxyphencyclimine Hydrochloride; Oxyphenonium Bromide; Ozagrel; Palauarnine; Palinavir; Palonosetron Hydrochloride; Pamaparin Sodium; Panamesine; Pancrelipase; Panipenem; Panipenum; Pannorin; Panornifene; Pantethine; Pantoprazole Sodium; Pantothenic Acid; Paramethadione; Paricalcitol; Parnaqueside; Parnicogrel; Paroxetine Hydrochloride; Paroxetine Mesylate; Parthenolide; Pazufloxacin; Pegademase Bovine; Pegvisomant; Pemirolast; Pemirolast Potassium; Penciclovir Sodium; Penicillamine; Pentafuside; Pentagastrin; Pentamidine; Pentamidine Isethionate; Pentetate Calcium Trisodium Yb-169; Pentigetide; Pentolinium Tartrate; Pentosan; Perflexane; Perfluoropolymethylisopropyl Ether; Perflutren; Pergolide; Pergolide Mesylate; Perindoprilat; Pernedolac; Perospirone; Phenaridine; Phenindione; Pheniramine Maleate; Phenmetrazine Hydrochloride; Phenotoxifvline; Phenserine; Phensuccinal; Phentermine Resin Complex; Phentolamine Mesilate; Phenylalanyl Ketoconazole; Phenylephrine Bitartrate; Phenytoin Sodium, Extended; Phenytoin Sodium, Prompt; Phosphoric Acid; Phytonadione; Picenadol; Picroliv; Picumeterol; Pidotimod; Pilsicainide; Pimagedine; Pimecrolimus; Pimilprost; Pinocebrin; Pioglitazone; Piperonyl Butoxide; Pirlindole; Pirmenol; Pirodornast; Polyestradiol Phosphate; Polyethylene Glycol 3350; Polytetrafluoroethylene; Poractant Alfa; Potassium Chloride; Pramipexole Dihydrochloride; Praziquantel; Prazosin; Prilocaine; Procaine Merethoxylline; Proguanil Hydrochloride; Propagermanium; Propentofylline; Propiolactone; Propiomazine Hydrochloride; Propionylcamitine, L-; Propiram; Propiram+ Paracetarnol; Propiverine; Prostratin; Protegrin; Protein Hydrolysate; Protokylol Hydrochloride; Protosufloxacin; Prulifloxacin; Pyrethrins; Pyridoxine; Pyridoxine Hydrochloride; Quazeparn; Quetiapine; Quetiapine Fumarate; Quiflapon; Quinagolide; Quinapril; Quinethazone; Quinidine Polygalacturonate; Raloxifene; Ramatroban; Ranelic Acid; Ranolazine; Rapacuronium Bromide; Recainarn; Regavirumab; Repaglinide; Rescinnamine; Resinferatoxin; Reticulon; Reviparin Sodium; Revizinone; Riboflavin; Riboflavin Phosphate Sodium; Ricasetron; Rilopirox; Rimantadine; Rimexolone; Rimoprogin; Riodipine; Ripisartan; Risedronic Acid; Rispenzepine; Ritipenem Acoxil; Ritipenern; Ritonavir; Rivastigmine Tartrate; Rizatriptan Benzoate; Rnibefradil; Rnivacurium Chloride; Rofecoxib; Rokitamycin; Ropinirole; Ropivacaine; Ropivacaine Hydrochloride Monohydrate; Roquinirnex; Rose Bengal Sodium, 1131; Rosiglitazone Maleate; Roxatidine; Roxindole; Rubidium Chloride Rb-82; Rufloxacin; Rupatidine; Ruzadolane; Sacrosidase; Safflower Oil; Safironil; Salbutamol, R—; Salnacedin, R—; Samarium Sm 153 Lexidronam Pentasodium; Sanfetrinem; Saprisartan; Sapropterin; Saquinavir; Sarcophytol A Sargramostim; Sarneridine; Sarnpatrilat; Sarpogrelate; Saruplase; Saterinone; Satigrel; Satumomab Pendetide; Scopolamine; Secretin; Selenomethionine, Se-75; Sematilide; Sermorelin; Sernotiadil; Sertaconazole; Sertraline; Sertraline-HCl; Setiptiline; Sevelamer Hydrochloride; Sevirurnab; Sezolamide; Sildenafil Citrate; Silipide; Silteplase; Silver Sulfadiazine; Simendan; Simethicone; Simethicone-Cellulose; Sinitrodil; Sinnabidol; Sipatrigine; Sirnvastatin; Somatomedin C; Somatropin Recombinant; Sorbitol; Sornatomedin B; Somatrem; Somatropin; Sotalol; Staurosporine; Stepronin; Stobadine; Strontium Chloride, Sr-89; Succibun; Sulfanilamide; Sulfaphenazole; Sulfapyridine; Sulfoxamine; Sulfoxone Sodium; Sulfur; Sultamicillin; Sultopride; Sumatriptan; Sutilains; Symakalim; Talbutal; Tandospirone; Tannic Acid; Tapgen; Taprostene; Tartaric Acid; Tazanolast; Tegaserod Maleate; Telenzepine; Telmesteine; Telmisartan; Temocapril; Tenofovir Disoproxil Fumarate; Tenosal; Tepirindole; Terazosin; Terbinafine Hydrochloride; Terflavoxate; Terguride; Terlipressin; Terodiline; Tertatolol; Testosterone Buciclate; Thallous Chloride, TI-201; Thiamine; Thiamine Hydrochloride; Thiofedrine; Thiomarinol; Thioperamide; Thiosemicarbazone; Thonzonium Bromide; Thyroglobulin; Thyrotropin; Thyrotropin Alfa; Tiagabine; Tiagabine Hydrochloride; Tianeptine; Tiapafant; Ticlopidine; Tienoxolol; Tilisolol; Tilnoprofen Arbamel; Tiludronic Acid; Tiopronin; Tiotropium Bromide; Tirandalydigin; Tirilazad; Tirofiban; Tiropramide; Tocopherol Acetate; Tolterodine Tartrate; Torasemide; Trafennin; Trandolapril; Tranylcypromine Sulfate; Travoprost; Traxanox; Trazodone-HCl; Treprostinil Sodium; Tretinoin Tocoferil; Triarntevene; Tricaprilin; Trichohyalin; Trichosanthin, Alpha; Triclosan; Tridihexethyl Chloride; Trientine; Trientine Hydrochloride; Triflavin; Trimegestone; Trimethoprim Hydrochloride; Trioxsalen; Triptorelin Pamoate; Trolamine Polypeptide Oleate Condensate; Trombodipine; Trometarnol; Tromethamine; Tropine Ester; Trospectomycin; Trovafloxacin; Trovafloxacin Mesylate; Trovirdine; Tucaresol; Tulobuterol; Tylogenin; Tyloxapol; Undecoylium Chloride; Undecoylium Chloride Iodine Complex; Unoprostone Isopropyl; Urapidil; Urea, C-13; Urea, C-14; Uridine Triphosphate; Valaciclovir; Valdecoxib; Valganciclovir Hydrochloride; Valproate Magnesium; Valproate Semisodium; Valrubicin; Valsartan; Vamicamide; Vanadeine; Vaninolol; Vasopressin Tannate; Venlafaxine; Verapamil, (S); Veratrum Viride; Veroxan; Vexibinol; Vinburnine Citrate; Vinburnine Resinate; Vinconate; Vinpocetine; Vinpocetine Citrate; Vintoperol; Viomycin Sulfate; Vitamin A; Vitamin A Palmitate; Vitamin E; Vitamin K; Voriconazole; Voxergolide; Warfarin Potassium; Xemilofiban; Ximoprofen; Yangarnbin; Zabicipril; Zacopride; Zacopride, R—; Zafirlukast; Zalospirone; Zaltoprofen; Zanamivir; Zanarnivir; Zankiren; Zatebradine; Zatosetron; Zenarestat; Zinostatin Stimalarner; Ziprasidone; Ziprasidone Mesylate; Zoledronic Acid; Zolmitriptan; Zolpidern; Zopiclone; Zopiclone, S—; Zopolrestat; and Zotepine.

Still other examples of therapeutically active agents are listed in 2000 MedAd News 19:56-60 and The Physicians Desk Reference, 53rd. Edition, pages 792-796, Medical Economics Company (1999).

The topical formulations of the present invention may include one or more skin care actives. "Skin care actives" means all compounds or substances now known or later demonstrated to provide benefit when applied to skin and all compounds now claimed or in the future claimed to provide benefit when applied to skin. Skin care actives may provide benefits, or claimed benefits, in areas such as one or more of wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-aging, reduction or avoidance of irritation and reduction or avoidance of inflammation. Examples of skin care actives include molecules such as peptides, proteins, oligonucleotides, fullerenes as well as small molecules. Skin care actives may be protease and/or enzyme inhibitors, anti-coenzymes, chelating agents, antibodies, antimicrobials, humectants, vitamins, skin protectants, antioxidants and/or skin soothing agents, plant extracts and the like. Examples of skin care actives include but are not limited to vitamin C, vitamin E (alpha tocopherol), retinoids, soy derivatives (e.g. isoflavones), green tea polyphenols, alpha hydroxy acids (e.g. glycolic and lactic acids), beta hydroxy acids (e.g. salicylic acid), poly hydroxy acids, alpha lipoic acid, hemp oil (glycerides), niacinamide, dimethyl amino ethanol, coenzyme Q10, kinetin (plant growth hormone), dimethyl sulfone and botulinum toxin. Other examples of skin care actives may be found in The Perricone Prescription by Nicholas Perricone, Harper Collins Publishers Inc., New York, 2002.

The topical formulations described herein may also include one or more cosmetically or pharmaceutically acceptable carriers/excipients. Suitable carriers/excipients that may be used in the topical formulations discussed herein are known in the art and include, but are not limited to, solubilizers such as $C_2$ to $C_8$ straight and branched chain alcohols, diols and triols, moisturizers and humectants such as glycerine, amino acids and amino acid derivatives, polyaminoacids and derivatives, pyrrolidone carboxylic acids and their salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrrolidone, polyvinyl alcohol and acrylic polymers. Other examples of suitable excipients, such as binders and fillers are listed in Remington's Pharmaceutical Sciences, 18th Edition, Ed. Alfonso Gennaro, Mack Publishing Co. Easton, Pa., 1995 and Handbook of Pharmaceutical Excipients, 3rd Edition, Ed. Arthur H. Kibbe, American Pharmaceutical Association, Washington, D.C. 2000.

The topical formulations of the present invention may also be formulated to include other chemical penetration enhancers which have significant ability to enhance transport of actives. Such substances may have the character of surfactants, a zone-like compounds, solvents, alcohols, fatty acids, fatty esters, aliphatic thiols and the like. Examples of chemical penetration enhancers are reported in the paper of Santus et al. (Santus, C. G. and Baker, R. W., Transdermal enhancer patent literature. Journal of Controlled Release 1993.25:1-20.)

The topical formulation of the present invention may be formulated by those skilled in the art as liquids, solutions, emulsions, creams, lotions, suspensions, triturates, gels, jellies, foams, pastes, ointments, shampoos, adhesives and the like.

The penetration enhancing effect may be measured using techniques known in the art. An example of one measurement method is described in the Examples below.

Preferably, the topical formulation includes at least one active agent such as a therapeutically effective agent or a skin care active. Examples of suitable active agents are described above. Preferably, the at least one active agent comprises a non-steroidal antiinflammatory drug (NSAID). Examples of suitable NSAIDs that may be used in the present topical formulation are described above. For example the formulation described above may include diclofenac, and particularly diclofenac sodium, as the at least one active agent.

The topical formulation described above may also include propylene glycol. The propylene glycol may be present in the formulation between about 1% to about 25% w/w. Additionally the topical formulation may also include ethanol and/or polyethylene glycol 300. The ethanol may be present in the formulation between about 1% to about 25% w/w. The polyethylene glycol 300 may be present in the range of between about 1% to about 80% w/w. In addition the topical formulation may include at least one moisturizer/humectant.

The present invention provides an improved topical formulation for preferably facilitating topical or transdermal administration of at least one therapeutically active agent. This enhanced effect is discussed further below and illustrated in preferred embodiments of the invention described in the Examples. In another preferred embodiment the topical formulation of the present invention provides a means for targeting a therapeutically active agent to local tissue either in the skin or the underlying tissue. This latter preferred embodiment may be particularly beneficially applied for treatment of conditions such as osteoarthritis and dermatological conditions. The topical formulations may be applied either occlusively or nonocclusively to the skin. In another preferred embodiment of the invention, in applications where the objective is transdermal administration of a therapeutically active agent to the systemic circulation, the topical formulation is applied to the skin under occlusion in a transdermal patch.

The present topical formulation may be applied to the skin by any means known in the art including, but not limited to, by an aerosol, spray, pump-pack, brush, swab, or other applicator. Preferably, the applicator provides either a fixed or variable metered dose application such as a metered dose aerosol, a stored-energy metered dose pump or a manual metered dose pump. Preferably the drug delivery system is applied to the skin of the human or animal covering a delivery surface area between about 10 and 800 $cm^2$, more preferably between about 10 and 400 $cm^2$, and most preferably about 10 and 200 $cm^2$. The application is most preferably performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. Preferably the area of application defined by the shroud is substantially circular in shape.

The drug delivery system may be a unit volume dispenser with or without a roll-on or other type of applicator. It may also be necessary to apply a number of dosages on untreated skin to obtain the desired result.

Embodiments of the invention will be described with reference to the following Examples which are provided for illustrative purposes only and should not be used to limit the scope of or construe the invention.

EXAMPLES

Materials and Methods for Examples 1-7

A number of formulations (described in Examples 1-7 below) containing diclofenac sodium (a non-steroidal antiinflammatory drug or NSAID) were tested for permeation through porcine skin using the Franz diffusion cells [as generally described in Franz T J: Percutaneous absorption. On the relevance of in vitro data. J. Invest Dermatol 1975; 64:190-195].

More specifically, Franz cells with a 5 ml receptor well volume were used in conjunction with full-thickness porcine skin harvested at Perry Scientific (San Diego, Calif.). The porcine skin was shaved free of hair, washed with water and subcutaneous fat was removed. The donor well had an area of ~0.5 cm²•Receptor wells were filled with isotonic phosphate buffered saline (PBS) doped with 0.01% sodium azide. The flanges of the Franz cell were coated with vacuum grease to ensure a complete seal and were clamped together with uniform pressure using a pinch clamp (SS #18 VWR 80073-350).

After the Franz cells were assembled, the porcine skin was allowed to pre-hydrate for 45 minutes with isotonic PBS. Isotonic PBS was then removed and 200 ml of the formulation was applied to the donor well. Receptor wells of the Franz cells were maintained at 37° C. (temperature on the surface of the skin is ~30° C.) in a stirring block with continual agitation via a stir bar.

The flux rates were calculated by assuming a radius of 0.4 cm in the donor well (i.e., an area of 0.503 cm²). The HPLC calibration curve for diclofenac was determined to have a slope of 115.6 AUC/(µg diclofenac/ml).

Samples were drawn from the receptor wells at t=24 hours and t=46 hours for all formulations. Franz diffusion cell measurements were made in five-fold replicates for each formulation.

The concentration of diclofenac in the samples was measured using HPLC analysis. Specifically, HPLC was carried out with C18 column and using acetonitrile and water as the mobile phase. Flux rates were calculated using standard equations based on the total transference of diclofenac across the skin after 46 hours. Thus, flux rates, F, were computed according to $$F = \frac{D*V}{t*A},$$

wherein: D is the concentration of the drug in the receptor well after incubation time t, V is the volume of the receptor well and A is the surface are of skin.

Individual penetration enhancers in the Examples discussed below were obtained from the following sources:
glyceryl oleate (glycerol monooleate) from TCI (VWR), product code TCG0082
isopropyl myristate from Sigma product code M0757
methyl laurate from Chem Service product code CS0426
N-lauroyl sarcosine from Sigma product code L5000
oleic acid (octadecenoic acid) from Mallinckroft (VWR) product code MK274404
sodium lauryl sulfoacetate from Stepan (65-72%) product code Lathanol LAL
sodium octyl sulfate from Alfa Aesar (VWR) product code AA43750-06

The base composition used for each formulation of a carrier composition comprising isotonic PBS, ethanol, propylene glycol and propylene glycol 300 in a volume ratio of 2:2:1:1. The base formulation further comprised diclofenac sodium in a concentration of 1.5 wt. % per unit volume of the base composition. In the Examples below, various combinations of the MPE™s detailed below were added to the base composition.

Example 1

In this Example, N-lauroyl sarcosine (NLS) and isopropyl myristate (IM) were added to the base formulation. The details of each formulation and the results of the Franz diffusion cell experiments are set out in Table 3.

With reference to Table 3, it can be seen that Formulation 2 (containing a mixture of NLS and IM each at a concentration 2.5% wt/vol.) was more effective at enhancing diclofenac sodium flux rates through the skin when compared to either of Formulation 3 (containing 5% wt./vol NLS and no IM) or Formulation 4 (containing 5% wt./vol IM and no NLS).

Further and surprisingly, Formulation 1 (containing a mixture of NLS and IM each at a concentration of 1.5% wt./vol) was approximately seven times more effective at enhancing the flux rate of the diclofenac sodium when compared to Formulation 2.

Example 2

In this Example, N-lauroyl sarcosine (NLS) and oleic acid (OA) were added to the base formulation. The details of each formulation and the results of the Franz diffusion cell experiments are set out in Table 4.

With reference to Table 4, it can be seen that Formulation 5 (containing a mixture of NLS and OA each at a concentration 1.5% wt/vol.) was more effective at enhancing diclofenac sodium flux rate through the skin when compared to either of Formulation 6 (containing 5% wt./vol NLS and no OA) or Formulation 7 (containing 5% wt./vol OA and no NLS).

It is notable that the flux rate of the NSAID in Formulation 5 was higher than that achieved by either of Formulation 6 or Formulation 7 in spite of the fact that the total concentration of the molecular penetration enhancers in Formulation 5 was lower that that in Formulation 6 and Formulation 7.

Example 3

In this Example, sodium octyl sulfate (SOS) and oleic acid (OA) were added to the base formulation. The details of each formulation and the results of the Franz diffusion cell experiments are set out in Table 5.

With reference to Table 5, it can be seen that Formulation 8 (containing a mixture of SOS and OA each at a concentration 1.5% wt/vol and 3.5% wt/vol, respectively) was more effective at enhancing diclofenac sodium flux rate through the skin when compared to either of Formulation 9 (containing 5% wt./vol OA and no SOS) or Formulation 10 (containing 5% wt./vol SOS and no OA).

Example 4

In this Example, glyceryl oleate (GO) and sodium octyl sulfate (SOS) were added to the base formulation. The details of each formulation and the results of the Franz diffusion cell experiments are set out in Table 6.

With reference to Table 6, it can be seen that Formulation 11 (containing a mixture of GO and SOS each at a concentration 1.5% wt/vol.) was approximately as effective at enhancing diclofenac sodium flux rate through the skin as Formulation 12 (containing 5% wt./vol GO and no SOS) and was substantially improved over that of Formulation 13 (containing 5% wt./vol SOS and no GO).

Example 5

In this Example, glyceryl oleate (GO) and methyl laurate (ML) were added to the base formulation. The details of each formulation and the results of the Franz diffusion cell experiments are set out in Table 7.

With reference to Table 7, it can be seen that Formulation 14 (containing a mixture of GO and ML each at a concentration 2.5% wt/vol.) was more effective at enhancing diclofenac sodium flux rate through the skin when compared to either of Formulation 15 (containing 5% wt./vol GO and no ML) or Formulation 16 (containing 5% wt./vol ML and no GO).

Example 6

In this Example, sodium lauryl sulfoacetate (SLSA) and methyl laurate (ML) were added to the base formulation. The details of each formulation and the results of the Franz diffusion cell experiments are set out in Table 8.

With reference to Table 8, it can be seen that Formulation 17 (containing a mixture of SLSA and ML each at a concentration 2.5% wt/vol.) was more effective at enhancing diclofenac sodium flux rate through the skin when compared to either of Formulation 18 (containing 5% wt./vol SLSA and no ML) or Formulation 19 (containing 5% wt./vol ML and no SLSA).

Example 7

In this Example, sodium lauryl sulfoacetate (SLSA) and isopropyl myristate (IM) were added to the base formulation. The details of each formulation and the results of the Franz diffusion cell experiments are set out in Table 9.

With reference to Table 9, it can be seen that Formulation 20 (containing a mixture of SLSA and IM each at a concentration 2.5% wt/vol.) was more effective at enhancing diclofenac sodium flux rate through the skin when compared to either of Formulation 21 (containing 5% wt./vol SLSA and no IM) or Formulation 22 (containing 5% wt./vol IM and no SLSA).

Materials and Methods for Example 8

Using methodology similar to that described in Examples 1-7, a number of formulations containing other active agents (as described in greater detail below) were tested for permeation through porcine skin using Franz diffusion cells.

Franz Cell Guidelines:

Skin preparation: Porcine skin was sourced from Lampire Biological Laboratories (Pipersville, Pa.). The skin was then dermatomed in house to a set thickness.

Diffusion cell assembly: Diffusion cells were assembled using dermatomed porcine skin as the substrate. Cell assembly was carried out by clamping the skin between a donor well (the flange was coated with a thin coating of vacuum grease to ensure a proper seal) and a receptor well. The wells were clamped together and held in place using a spring clamp.

The receptor wells had a volume of 3.3ml and the clamped skin had an available surface area of ~0.55 cm$^2$ for the diffusion study. Once the cell was assembled, the receptor well was filled with PBS containing 0.01 wt % NaN$_3$ (to help prevent skin degradation). Care was taken to ensure all bubbles are removed from the receptor solution. The skin was allowed to pre-hydrate for 20 minutes before the formulations were applied to the skin.

Diffusion cell testing: After the skin was prehydrated, 40 μl of the test formulation was applied to the skin with a positive displacement pipettor and the applied dose then rubbed gently across the skin with a glass stir rod. Once the formulation was applied, a stir bar was added to the receptor well. The receptor well was maintained at 32° C. and continuously agitated throughout the experiment. Sample aliquots were drawn from the receptor well at varying time points and replaced with fresh PBS buffer. Sample aliquots were filtered and analyzed for concentration of the active using HPLC analysis. Measurements for each formulation were carried out in six-fold replicates.

The individual penetration enhancers used in Example 8 are provided in the following table along with their abbreviation (Abbr) and Chemical Abstract Service (CAS) registry number:

| Abbr | Chemical | CAS |
|------|----------|-----|
| IM | Isopropyl Myristate | 110-27-0 |
| SLSA | Sodium Lauryl Sulfoacetate | 1847-58-1 |
| OA | Oleic Acid | 112-801-1 |
| ML | Methyl Laurate | 111-82-0 |
| GO | Glyceryl Monooleate | 31566-31-1 |
| NLS | N-lauroyl Sarcosine | 97-78-9 |

Numerous formulations were prepared with the MMPE™s used in conjunction with varying active agents. MMPE™s tested were SLSA/IM, SLSA/ML, IM/NLS, GO/ML, and NLS/OA in a hydroalcoholic solution. These MMPE™s were tested with the active agents ibuprofen, buprorion HCl, ketoprofen and testosterone. Tables 10-19 list the MMPE™s that showed a significant increase in flux when compared to flux from the analogous formulations containing only one of the MPE™s.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

All publications, patents and patent applications referred to herein are incorporated by reference in their entirety to the same extent as if each individual publication, patent or patent application was specifically and individually indicated to be incorporated by reference in its entirety.

TABLE 1

| NSAID | TRADE NAME | STRUCTURE |
|-------|-----------|-----------|
| Diclofenac | Voltaren, Pennsaid | 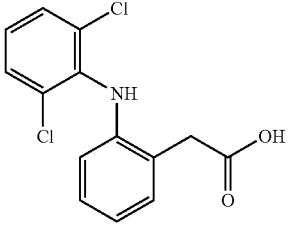 [SMILES: O=C(O)Cc1ccccc1Nc1c(Cl)cccc1Cl] |

TABLE 1-continued
| NSAID | TRADE NAME | STRUCTURE |
|---|---|---|
| Indomethacin | Indocin | 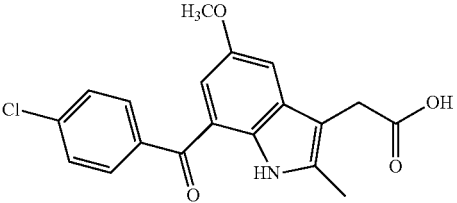 [SMILES: COc1cc(C(=O)c2ccc(Cl)cc2)c2[nH]c(C)c(CC(=O)O)c2c1] |
| Sulindac | Clinoril | 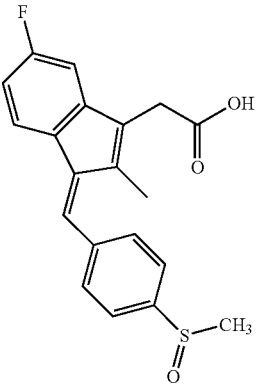 [SMILES: CC1=C(CC(=O)O)c2cc(F)ccc2/C1=C/c1ccc(S(C)=O)cc1] |
| Tolmetin | Tolectin | 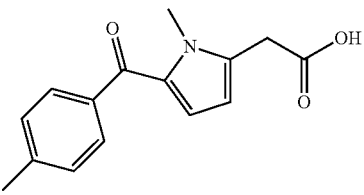 [SMILES: Cc1ccc(C(=O)c2ccc(CC(=O)O)n2C)cc1] |
| Naproxen | Naprosyn, Aleve | 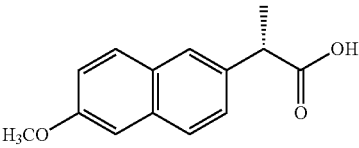 [SMILES: COc1ccc2cc([C@H](C)C(=O)O)ccc2c1] |
| Ibuprofen | Advil, Brufen, Motrin | 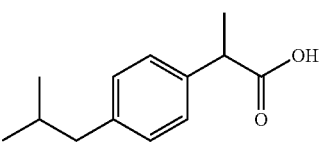 |
| Flurbiprofen | Ansaid, Flurwood, Froben | 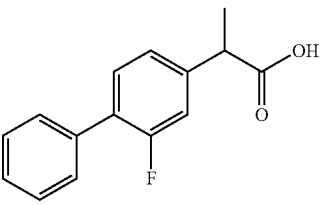 [SMILES: CC(C(=O)O)c1ccc(-c2ccccc2)c(F)c1] |
| Ketoprofen | Orudis | 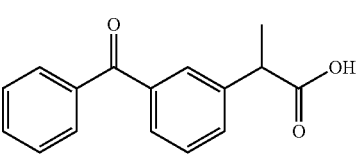 [SMILES: CC(C(=O)O)c1cccc(C(=O)c2ccccc2)c1] |

TABLE 1-continued
| NSAID | TRADE NAME | STRUCTURE |
|---|---|---|
| Ketorolac | Acular, Toradol | 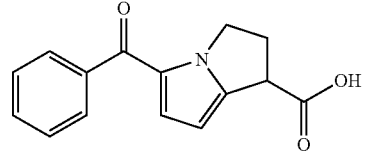 [SMILES: O=C(c1ccccc1)c1ccc2n1CCC2C(=O)O] |
| Fenoprofen | Nalfon | 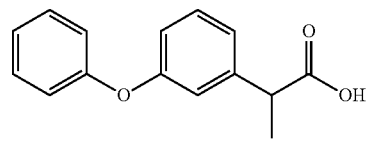 [SMILES: CC(C(=O)O)c1cccc(Oc2ccccc2)c1] |
| Bromfenac | Xibrom | 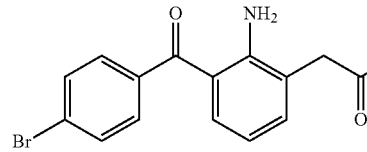 |
TABLE 2
| COMPOUND | TRADE NAME | STRUCTURE |
|---|---|---|
| Acetaminophen | Tylenol | 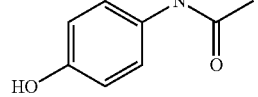 |
| Aspirin | | 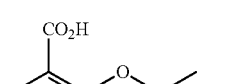 |
| Celecoxib | Celebrex | 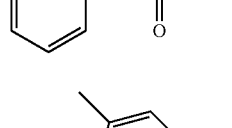 |
| Diflunisal | Dolobid | 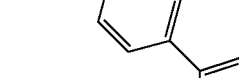 |

TABLE 2-continued

| COMPOUND | TRADE NAME | STRUCTURE |
|---|---|---|
| Etoricoxib | Arcoxia | 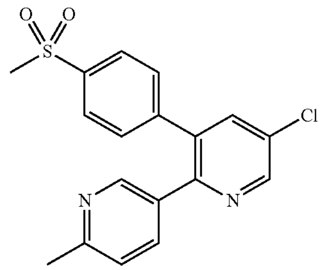 [SMILES: Cc1ccc(-c2ncc(Cl)cc2-c2ccc(S(C)(=O)=O)cc2)cn1] |
| Piroxicam | Feldane, Roxam | 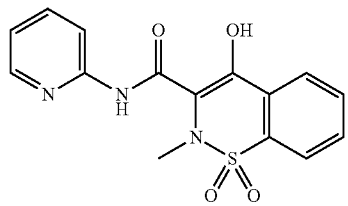 [SMILES: CN1C(C(=O)Nc2ccccn2)=C(O)c2ccccc2S1(=O)=O] |
| Rofecoxib | Vioxx | 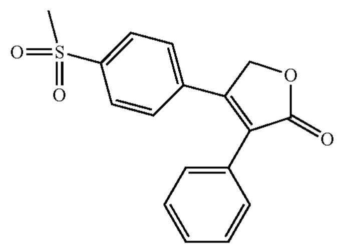 [SMILES: CS(=O)(=O)c1ccc(C2=C(c3ccccc3)C(=O)OC2)cc1] |
| Salsalate | Disalcid, Monogesic, Salflex, Salcitab | 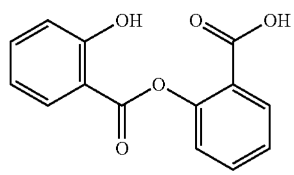 [SMILES: O=C(Oc1ccccc1C(=O)O)c1ccccc1O] |
| Meloxicam | Mobic | 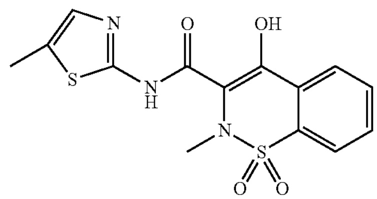 [SMILES: Cc1cnc(NC(=O)C2=C(O)c3ccccc3S(=O)(=O)N2C)s1] |
| Etodolac | Lodine | 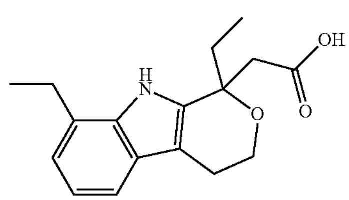 [SMILES: CCc1cccc2c3c([nH]c12)C(CC)(CC(=O)O)OCC3] |
| Oxaprozin | Daypro | 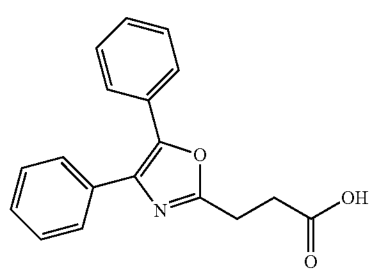 [SMILES: O=C(O)CCc1nc(-c2ccccc2)c(-c2ccccc2)o1] |

TABLE 2-continued

| COMPOUND | TRADE NAME | STRUCTURE |
|---|---|---|
| Nabumetone | Relafen | (structure) |
| Mefenamic acid | Ponstel | (structure) |
| Meclofenamic Acid | Meclofen, Meclomen | (structure) |

TABLE 3

| Formulation | [NLS + IM] (wt. %/vol.) | Weight Ratio of NLS:IM | Flux (µg/hr/cm$^2$) |
|---|---|---|---|
| 1 | 3.0 | 1:1 | 3.80 |
| 2 | 5.0 | 1:1 | 0.53 |
| 3 | 5.0 | 1:0 | 0.26 |
| 4 | 5.0 | 0:1 | 0.02 |

TABLE 4

| Formulation | [NLS + OA] (wt. %/vol.) | Weight Ratio of NLS:OA | Flux (µg/hr/cm$^2$) |
|---|---|---|---|
| 5 | 3.0 | 1:1 | 3.29 |
| 6 | 5.0 | 1:0 | 0.26 |
| 7 | 5.0 | 0:1 | 2.70 |

TABLE 5

| Formulation | [SOS + OA] (wt. %/vol.) | Weight Ratio of SOS:OA | Flux (µg/hr/cm$^2$) |
|---|---|---|---|
| 8 | 5.0 | 3:7 | 4.73 |
| 9 | 5.0 | 0:1 | 2.70 |
| 10 | 5.0 | 1:0 | 0.02 |

TABLE 6

| Formulation | [GO + SOS] (wt. %/vol.) | Weight Ratio of GO:SOS | Flux (µgl/hr/cm$^2$) |
|---|---|---|---|
| 11 | 3.0 | 1:1 | 0.30 |
| 12 | 5.0 | 1:0 | 0.34 |
| 13 | 5.0 | 0:1 | 0.02 |

TABLE 7

| Formulation | [GO + ML] (wt. %/vol.) | Weight Ratio of GO:ML | Flux (µg/hr/cm$^2$) |
|---|---|---|---|
| 14 | 5.0 | 1:1 | 0.54 |
| 15 | 5.0 | 1:0 | 0.34 |
| 16 | 5.0 | 0:1 | 0.32 |

TABLE 8

| Formulation | [SLSA + ML] (wt. %/vol.) | Weight Ratio of SLSA:ML | Flux (µg/hr/cm$^2$) |
|---|---|---|---|
| 17 | 5.0 | 3:7 | 0.52 |
| 18 | 5.0 | 1:0 | 0.22 |
| 19 | 5.0 | 0:1 | 0.32 |

TABLE 9

| Formulation | [SLSA + IM] (wt. %/vol.) | Weight Ratio of SLSA:IM | Flux (µg/hr/cm$^2$) |
|---|---|---|---|
| 20 | 5.0 | 1:1 | 0.52 |
| 21 | 5.0 | 1:0 | 0.22 |
| 22 | 5.0 | 0:1 | 0.02 |

TABLE 10

| Formulation | Ibuprofen (wt/wt %) | SLSA (wt/wt %) | IM (wt %/wt %) | Flux (µg/hr/cm$^2$) |
|---|---|---|---|---|
| 23 | 5 | 3 | | 42.1 |
| 24 | 5 | | 3 | 28.5 |
| 25 | 5 | 1.5 | 1.5 | 66.5 |

TABLE 11

| Formulation | Ibuprofen (wt %/wt %). | SLSA (wt %/wt %). | ML (wt %/wt %). | Flux (μg/hr/cm²) |
|---|---|---|---|---|
| 26 | 5 | 3 | | 42.1 |
| 27 | 5 | | 3 | 25.2 |
| 28 | 5 | 1.5 | 1.5 | 53.9 |

TABLE 12

| Formulation | Ibuprofen (wt %/wt %). | IM (wt %/wt %). | NLS (wt %/wt %). | Flux (μg/hr/cm²) |
|---|---|---|---|---|
| 29 | 5 | 3 | | 28.5 |
| 30 | 5 | | 3 | 10.0 |
| 31 | 5 | 1.5 | 1.5 | 31.0 |

TABLE 13

| Formulation | Ibuprofen (wt %/wt %). | GO (wt %/wt %). | ML (wt %/wt %). | Flux (μg/hr/cm²) |
|---|---|---|---|---|
| 32 | 5 | 3 | | 14.4 |
| 33 | 5 | | 3 | 25.2 |
| 34 | 5 | 1.5 | 1.5 | 53.6 |

TABLE 14

| Formulation | Bupropion HCl (wt %/wt %). | NLS (wt %/wt %). | OA (wt %/wt %). | Flux (μg/hr/cm²) |
|---|---|---|---|---|
| 35 | 5 | 3 | | 14.3 |
| 36 | 5 | | 3 | 9.1 |
| 37 | 5 | 1.5 | 1.5 | 18.8 |

TABLE 15

| Formulation | Bupropion HCl (wt %/wt %). | SLSA (wt %/wt %). | IM (wt %/wt %). | Flux (μg/hr/cm²) |
|---|---|---|---|---|
| 38 | 5 | 3 | | 34.3 |
| 39 | 5 | | 3 | 14.5 |
| 40 | 5 | 1.5 | 1.5 | 45.6 |

TABLE 16

| Formulation | Bupropion HCl (wt %/wt %). | SLSA (wt %/wt %). | ML (wt %/wt %). | Flux (μg/hr/cm²) |
|---|---|---|---|---|
| 41 | 5 | 3 | | 34.3 |
| 42 | 5 | | 3 | 14.8 |
| 43 | 5 | 1.5 | 1.5 | 51.3 |

TABLE 17

| Formulation | Bupropion HCl (wt %/wt % l). | IM (wt %/wt %). | NLS (wt %/wt %). | Flux (μg/hr/cm²) |
|---|---|---|---|---|
| 44 | 5 | 3 | | 14.5 |
| 45 | 5 | | 3 | 14.3 |
| 46 | 5 | 1.5 | 1.5 | 55.9 |

TABLE 18

| Formulation | Ketoprofen (wt %/wt % l). | NLS (wt %/wt %). | OA (wt %/wt % l). | Flux (μg/hr/cm²) |
|---|---|---|---|---|
| 47 | 5 | 3 | | 14.3 |
| 48 | 5 | | 3 | 9.1 |
| 49 | 5 | 1.5 | 1.5 | 18.8 |

TABLE 19

| Formulation | Testosterone (wt %/wt %). | SLSA (wt %/wt %). | IM (wt %/wt %). | Flux (μg/hr/cm²) |
|---|---|---|---|---|
| 50 | 5 | 3 | | 14.3 |
| 51 | 5 | | 3 | 9.1 |
| 52 | 5 | 1.5 | 1.5 | 18.8 |

What is claimed is:

1. A topical formulation comprising: (i) at least one active agent, (ii) a first compound, and (iii) a second compound, wherein the first compound and second compound are different, and each is selected from the group consisting of N-lauroyl sarcosine, sodium octyl sulfate, methyl laurate, isopropyl myristate, oleic acid, glyceryl oleate and sodium lauryl sulfoacetate.

2. The topical formulation of claim 1, wherein the first compound comprises sodium lauryl sulfoacetate and the second compound comprises isopropyl myristate.

3. The topical formulation of claim 1, wherein the first compound comprises sodium lauryl sulfoacetate and the second compound comprises methyl laurate.

4. The topical formulation of claim 1, wherein the first compound comprises isopropyl myristate and the second compound comprises N-lauryl sarcosine.

5. The topical formulation of claim 1, wherein the first compound comprises glyceryl monooleate and the second compound comprises methyl laurate.

6. The topical formulation of claim 1, wherein the first compound comprises N-lauroyl sarcosine and the second compound comprises oleic acid.

7. The topical formulation of claim 1, wherein the first compound comprises sodium octyl sulfate and the second compound comprises oleic acid.

8. The topical formulation of claim 1, wherein the first compound comprises glyceryl oleate and the second compound comprises sodium octyl sulfate.

9. The topical formulation of claim 1, further comprising a biologically acceptable excipient.

10. The topical formulation of claim 1, wherein the total concentration of the first compound and the second compound is up to about 50 wt. %, 40 wt. %, 35 wt. %, 30 wt. %, 25 wt %, 20 wt. %, 15 wt. %, 10 wt. %, 7.5 wt. % or 5 wt. %, per unit volume of the formulation.

11. The topical formulation of claim 1, wherein the total concentration of the first compound and the second compound is in the range of from about 2 wt. % to about 5 wt %, per unit volume of the formulation.

12. The topical formulation of claim 1, wherein the total concentration of the first compound and the second compound is in the range of from about 2 wt. % to about 4 wt %, per unit volume of the formulation.

13. The topical formulation of claim 1, wherein the weight ratio of the first compound to the second compound is in the range of from about 1:9 to about 9:1.

14. The topical formulation of claim 1, wherein the weight ratio of the first compound to the second compound is in the range of from about 1:4 to about 4:1.

15. The topical formulation of claim 1, wherein the weight ratio of the first compound to the second compound is in the range of from about 1:3 to about 3:1.

16. The topical formulation of claim 1, wherein the weight ratio of the first compound to the second compound is in the range of from about 1:2 to about 2:1.

17. The topical formulation of claim 1, wherein the weight ratio of the first compound to the second compound is about 1:1.

18. The topical formulation of claim 1, wherein the at least one active agent is an α-aryl alkanoic acid.

19. The topical formulation of claim 18, wherein the α-aryl alkanoic acid is an anti-inflammatory drug, such as a non-steroidal anti-inflammatory drug (NSAID), or an analgesic.

20. The topical formulation of claim 18, wherein the α-aryl alkanoic acid is selected from the group consisting of bromfenac, diclofenac, fenoprofen, flurbiprofen, ibuprofen, indomethacin, ketoprofen, ketorolac, naproxen, sulindac and tolmetin, and pharmaceutically acceptable salts and solvates thereof and mixtures thereof.

21. The topical formulation of claim 20, wherein the α-aryl alkanoic acid is selected from the group consisting of diclofenac, ibuprofen and ketoprofen, and pharmaceutically acceptable salts and solvates thereof, and mixtures thereof.

22. The topical formulation of claim 1, wherein the at least one active agent is acetaminophen or an NSAID selected from the group consisting of aspirin, celecoxib, diflunisal, etodolac, etoricoxib, meclofenamic acid, mefenamic acid, meloxicam, nabumetone, oxaprozin, piroxicam, salsalate, and rofecoxib, and pharmaceutically acceptable salts and solvates thereof, and mixtures thereof.

23. The topical formulation of claim 1, wherein the at least one active agent is a phenethylamine.

24. The topical formulation of claim 23, wherein the phenethylamine is selected from the group consisting of antidepressants, anti-anxiety agents, anticholinergic agents, cholinergics, dopaminergics, stimulants, serotonin antaogonists, serotonin inhibitors, anti-emetics, antihistamines and/or antipsychotics.

25. The topical formulation of claim 24, wherein the phenethylamine is selected from the group consisting of bupropion, amphetamine, hydroxyamphetamine, dextroamphetamine, methamphetamine, ephedrine, epinephrine, pseudoephedrine, dopamine, epinephryl borate, etafedrine, norepinephrine and oxidopamine, and pharmaceutically acceptable salts and solvates thereof, and mixtures thereof.

26. The topical formulation of claim 25, wherein the phenethylamine is bupropion or a pharmaceutically acceptable salt or solvate thereof.

27. The topical formulation of claim 1, wherein the at least one active agent is a steroid.

28. The topical formulation of claim 27, wherein the steroid is selected from the group consisting of hormones, glucosteroids, androgens, adrenocortical steroids, anabolics, estrogens and/or progestin.

29. The topical formulation of claim 27, wherein the steroid is testosterone or a pharmaceutically acceptable salt or solvate thereof.

* * * * *